(12) United States Patent
Martakos et al.

(10) Patent No.: US 6,923,927 B2
(45) Date of Patent: *Aug. 2, 2005

(54) METHOD FOR FORMING EXPANDABLE POLYMERS HAVING DRUGS OR AGENTS INCLUDED THEREWITH

(75) Inventors: Paul Martakos, Pelham, NH (US); Roger Labrecque, Londonderry, NH (US); Geoffrey Moodie, Hudson, NH (US); Steve A. Herweck, Nashua, NH (US); Theodore Karwoski, Hollis, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/807,709

(22) Filed: Mar. 23, 2004

(65) Prior Publication Data

US 2004/0232587 A1 Nov. 25, 2004

Related U.S. Application Data

(63) Continuation-in-part of application No. 10/131,446, filed on Apr. 22, 2002, which is a continuation-in-part of application No. 09/678,765, filed on Oct. 3, 2000, now Pat. No. 6,616,876.

(51) Int. Cl.[7] .......................... B29B 11/10; B29B 11/14; B29B 13/00; B29B 13/02; B29B 15/00
(52) U.S. Cl. ....................... 264/119; 264/122; 264/123; 264/126; 264/120; 264/241; 264/291
(58) Field of Search ................................ 264/119, 122, 264/123, 126, 120, 241, 291

(56) References Cited

U.S. PATENT DOCUMENTS 3,862,030 A   1/1975   Goldberg 4,177,334 A   12/1979   Okita (Continued)

FOREIGN PATENT DOCUMENTS

| EP | 0 106 496 B2 | 4/1984 |
|----|---|---|
| EP | 0 288 021 B1 | 10/1988 |

(Continued)

OTHER PUBLICATIONS

Libby P. Atherosclerosis: the new view. Sci Am. May 2002;286(5):46–55.

*Primary Examiner*—Stephen J. Lechert, Jr.
(74) *Attorney, Agent, or Firm*—Lahive & Cockfield, LLP

(57) ABSTRACT

The invention is directed to methods involving rewetting of expandable polymers with a wettable liquid to allow for enhanced expansion at or below room temperature without breakage, and in some cases, allows one to achieve a greater expansion ratio than that allowed at elevated temperatures using known methods. The wettable liquid can be formed of a drug and/or an agent, such that the resulting polymer contains and emits the drug upon positioning at a target location of a patient body. The expandable polymer can also have the drug or agent added to its structure at a polymer resin preparation stage, through use of an aqueous solution mixed with one or more fluoropolymers, or in a mixing stage. The present invention also allows one to achieve material with unique properties and handling characteristics. These properties included decreased material thickness, increased density, an altered node/fibril morphology, and a more consistent web in the case of flat material. This method is not limited to room temperature conditions and can be applied whenever the expandable polymer material is wet with a wettable liquid, and the expansion is performed at a temperature preferably below the vaporization or boiling points of that liquid.

92 Claims, 21 Drawing Sheets

U.S. PATENT DOCUMENTS

| | | | |
|---|---|---|---|
| 4,187,390 A | | 2/1980 | Gore |
| 4,598,011 A | | 7/1986 | Bowman |
| 4,938,911 A | | 7/1990 | Bastiaansen et al. |
| 5,064,593 A | | 11/1991 | Tamaru et al. |
| 5,080,899 A | | 1/1992 | Sturm et al. |
| 5,288,711 A | | 2/1994 | Mitchell et al. |
| 5,411,550 A | | 5/1995 | Herweck et al. |
| 5,476,589 A | | 12/1995 | Bacino |
| 5,516,781 A | | 5/1996 | Morris et al. |
| 5,552,100 A | | 9/1996 | Shannon et al. |
| 5,641,373 A | | 6/1997 | Shannon et al. |
| 5,721,283 A | | 2/1998 | Howard, Jr. et al. |
| 5,756,035 A | * | 5/1998 | Underwood et al. ........ 264/295 |
| 5,788,626 A | | 8/1998 | Thompson |
| 5,800,522 A | | 9/1998 | Campbell et al. |
| 5,824,050 A | | 10/1998 | Karwoski et al. |
| 5,843,173 A | | 12/1998 | Shannon et al. |
| 5,853,419 A | | 12/1998 | Imran |
| 5,897,587 A | | 4/1999 | Martakos et al. |
| 5,964,798 A | | 10/1999 | Imran |
| 5,976,169 A | | 11/1999 | Imran |
| 6,022,374 A | | 2/2000 | Imran |
| 6,153,252 A | | 11/2000 | Hossainy et al. |
| 6,159,531 A | | 12/2000 | Dang et al. |
| 6,231,600 B1 | | 5/2001 | Zhong |
| 6,273,913 B1 | | 8/2001 | Wright et al. |
| 6,355,063 B1 | | 3/2002 | Calcote |
| 6,364,856 B1 | | 4/2002 | Ding et al. |
| 6,364,903 B2 | | 4/2002 | Tseng et al. |
| 6,368,626 B1 | | 4/2002 | Bhatt et al. |
| 6,613,082 B2 | | 9/2003 | Yang |
| 6,613,084 B2 | | 9/2003 | Yang |
| 2004/0142094 A1 | | 7/2004 | Narayanan |

FOREIGN PATENT DOCUMENTS

| | | |
|---|---|---|
| JP | 54086573 | 7/1979 |
| JP | 06071744 | 3/1994 |
| WO | WO 98/26731 A2 | 6/1998 |
| WO | WO 00/12147 A1 | 3/2000 |
| WO | WO 01/15764 A1 | 3/2001 |
| WO | WO 01/21106 A1 | 3/2001 |
| WO | WO 01/82833 A2 | 11/2001 |
| WO | WO 02/26279 A1 | 4/2002 |
| WO | WO 02/36054 A1 | 5/2002 |

* cited by examiner

METHOD FOR FORMING EXPANDABLE POLYMERS HAVING DRUGS OR AGENTS INCLUDED THEREWITH

RELATED APPLICATIONS

This application is a continuation-in-part of, and claims the benefit of U.S. patent application Ser. No. 10/131,446, filed Apr. 22, 2002, which is expressly and entirely incorporated herein by reference, and which was a continuation-in-part of, and claimed the benefit of, U.S. patent application Ser. No. 09/678765, filed Oct. 3, 2000, now U.S. Pat. No. 6,616,876, which issued Sep. 9, 2003.

TECHNICAL FIELD

The present invention relates generally to materials and processing of materials. More specifically, the present invention is directed to expandable polymers and methods for processing of expandable polymers.

BACKGROUND

A conventional method of forming an article made of an expandable polymer, such as PTFE, is to blend a powdered resin with a wettable liquid, such as a lubricant or extrusion aid, and compress the combination under relatively low pressure into a preformed billet. A wettable liquid is mixed with the powdered resin to control the degree of material shear that occurs during subsequent extrusion and to prevent excessive shear, which can damage the material.

Using a ram-type extruder, the billet is extruded through a die having a desired cross-section. Next, the wettable liquid is removed from the extruded material by drying or by another extraction method. The dried extruded material is then stretched in one or more directions at an elevated temperature below the crystalline melting point of the resin. In the case of PTFE, this results in the material taking on a microstructure characterized by elongated nodes interconnected by fibrils. Typically, the nodes are oriented with their elongated axis perpendicular to the direction of stretching.

According to conventional methods, there is a direct relationship between temperature and maximum expansion ratio while maintaining material uniformity and without breakage of the material. At low expansion temperatures, the material shows inconsistencies, is weak, and often breaks. Typically, heating well above room temperature is required to prevent the expandable polymer material from breaking and to ensure uniform material thickness after expansion.

U.S. Pat. No. 4,187,390 describes a method of forming porous PTFE that requires stretching at elevated temperatures. Material expanded at lower temperatures often fractures or results in weak material.

U.S. Pat. No. 5,552,100 describes a method of forming thin porous fluoropolymer films by post-sinter stretching the material to a final thickness less than 0.002 inches. The conventional manufacturing of films having thicknesses below 0.002 inches during pre-sinter expansion often results in breaking or tearing of the film.

Conventional methods of processing expanded polymers, such as PTFE (polytetrafluoroethylene), PET (polyethylene terephthalate), and UHMWPE (ultra high molecular weight polyethylene), require high temperatures and pressures as discussed. These high temperatures and pressures are not conducive to inclusion of a drug or active agent during the process of expansion. Such conditions have deleterious effects on the drugs and agents.

Therefore, a need exists for a method providing substantial expansion of expandable polymers, without need for heating, to create uniform material with alternate polymer morphologies. Furthermore, the ability to decrease thickness, increase strength, uniformity and density of expandable polymers is desirable in many applications. In addition, the ability to include a drug or otherwise active agent in the expandable polymer is desirable to enable the application of the drug or agent to targeted locations requiring treatment.

SUMMARY

The present invention is directed generally to methods for treating expandable polymers and products produced therefrom. More particularly, the invention relates to methods for forming an article from an expandable polymer that has been stretched involving the steps of rewetting the expandable polymer with a wettable liquid to form a wetted material, and stretching the wetted material. The wettable liquid can later be removed.

The wettable liquid can be formed at least partially with a drug or agent. The drug or agent intersperses throughout at least a portion of the expandable polymer during the wetting and/or re-wetting processes.

According to another aspect of the invention, an article is formed by rewetting an expandable polymer and then stretching the expandable polymer. Expandable polymer articles formed in accordance with the processes of the invention have characteristics, such as uniformity, porosity, density, node size, thickness, fibril density and permeability not attainable from conventional methods. The method of the present invention provides for an increased drug loading capacity relative to conventional drug incorporation methods, such as immersion and impregnation.

In accordance with one embodiment of the present invention, a method is provided for forming an article. The method includes mixing a polymer resin with a first wettable liquid and at least one of a drug and an agent to form a mixture. A pre-form is formed from the mixture. The pre-form is extruded to form the article. The extruded article can alternatively be stretched to form the article. The extruded article can also be dried prior to stretching, or re-wetted prior to, or after, stretching. According to a further aspect, the extruded article can be re-wetted, stretched, and re-wetted again.

In accordance with another embodiment of the present invention, a method is provided for forming an article. The method includes mixing an aqueous dispersion of fluoropolymer with at least one of a drug and an agent to form a mixture. The mixture is coagulated. A pre-form is created from the mixture, and the pre-form is extruded to form the article. In accordance with further aspects of the present invention, the extruded article can be stretched to create the article. The extruded article can be dried, or re-wetted, prior to or after stretching, as well.

In accordance with another embodiment of the present invention, a method is provided for forming an article. The method includes mixing a polymer resin with a first wettable liquid and at least one of a drug and an agent to form a mixture. A pre-form is created from the mixture. The pre-form is extruded to form an extruded article. The extruded article is stretched, and then re-wetted with a second wettable liquid including at least one of a drug and an agent to form the article. The re-wetted article can also be subsequently stretched again.

In accordance with another embodiment of the present invention, a method for forming an article is provided. The method includes combining at least one of a drug and an agent with a first wettable liquid. A polymer resin is mixed with the first wettable liquid to form a mixture. A pre-form is created from the mixture. The pre-form is extruded to form an extruded article. A low BP component is dried from the wettable liquid of the extruded article. The extruded article is stretched to form the article.

These and other features, aspects, and advantages of the present invention will become better understood with reference to the following description and appended claims.

BRIEF DESCRIPTION OF THE DRAWINGS

The present invention will become better understood with reference to the following description and accompanying drawings, wherein.

DETAILED DESCRIPTION

Figure 1:
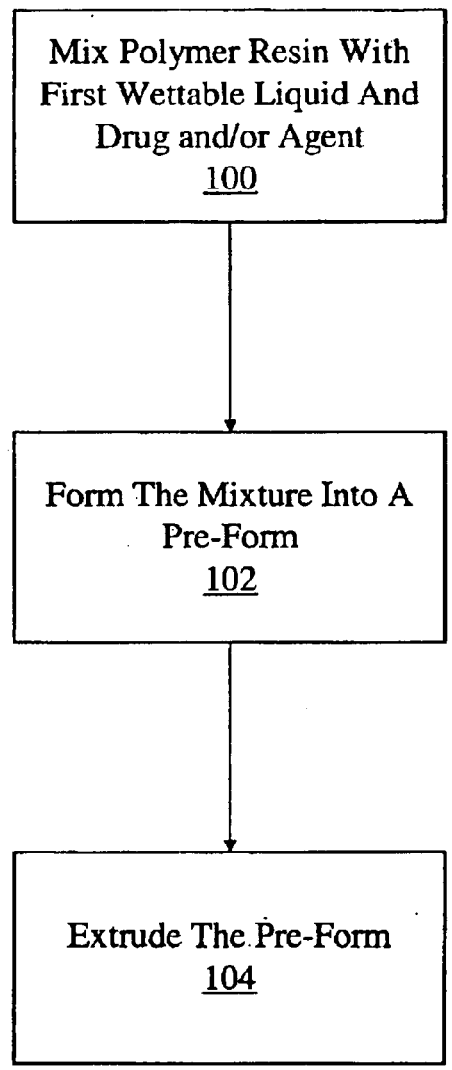
FIG. 1 is a flowchart illustrating one example method for forming an article according to one embodiment of the present invention.

The present invention provides a means for expanding expandable polymers at or below room temperature without breakage and maintaining a substantially uniform material, and allows one to achieve a greater expansion ratio than that allowed at elevated temperatures using known methods. Furthermore, the present invention provides a method for inclusion of a drug or active agent in the composition of the expanded polymers. The expanded polymers can be formed into a plurality of different devices and utilized to apply the drug or active agent in a targeted and/or time extended manner. In addition, the method of the present invention provides for an increased drug loading capacity relative to conventional drug incorporation methods, such as immersion and impregnation.

Polymers with ordered microstructures, often referred to as highly crystalline, have the fundamental ability to expand into another shape and size. Fluoropolymers and polyolefins are polymers suitable for expansion processes. Fluoropolymers include homopolymers of polytetrafluoroethylene (PTFE), and copolymers of polytetrafluoroethylene in which the co-monomer is ethylene, chlorotrifluoroethylene, perfluoroalkoxytetrafluoroethylene, and fluorinated propylene. Polyolefins include polypropylene and polyethylene.

The concepts of contact angle and its equilibrium are useful for the present discussion because these concepts can be used to define wettability. When a liquid wets a solid, the liquid spreads freely over the surface at a rate depending on the liquid viscosity, surface tension of the liquid, roughness of the solid surface, porosity of the solid surface, and chemistry. The tendency for the liquid to spread increases as contact angle decreases so contact angle is a useful inverse measure of wettability. Contact angle is the angle that the liquid makes with a solid. The contact angle of a liquid is a result of the thermodynamic equilibrium of a drop on a solid surface. At the interface between a liquid and solid, the interfacial monolayer of the liquid is attracted by the bulk liquid and gas from one side and from the other side by the intermolecular forces, which interact between the solid and liquid. A porous material is said to be "wet" when the voids of the material are at least partially occupied by a given fluid.

In accordance with the present invention, multi-directional expansion of an expandable polymer (sintered or unsintered) can occur at room temperature provided the material is rewet with a wettable liquid before or during the expansion step. Rewetting involves the application of wettable liquid after completion of activities for which wettable liquid may be used. Removal of any previous wettable liquid is not required before rewetting. This method is not limited to room temperature conditions and can be applied whenever the expandable polymer is wet with the wettable liquid. Ideally, the expansion is performed at a temperature below the vaporization or boiling points of the wettable liquid.

The phrase "wet stretch" refers to the expansion or deformation of an expandable polymer in one or more directions when the material is wet with a wettable liquid before or during the expansion step. Wet stretching of an expandable polymer resin, such as PTFE, can provide: modified processability, material structures which differ from those made from conventionally processed resin (for example, decreased thickness, increased density, and product uniformity). The overall feel of the product is typically enhanced, due to increased smoothness.

Major differences can be seen between the structures produced according to the invention and those produced with conventional methods. The resulting products have increased density and improved strength, allowing the products to be thinner than those made from conventional methods.

The extrudate may also be sintered, after stretching or before stretching, by heating it to a temperature above its crystalline melting point while being maintained in a stretched condition. This can be considered an amorphous locking process for permanently "locking-in" the microstructure in the expanded or stretched configuration. The methods of the invention can simultaneously provide greatly reduced sintering times and improved product structure over conventional methods. The present invention does not require sintering for certain applications, including endovascular, filtration, and the like, as is typically required by conventional methods. In addition, sintering can be utilized in the present invention in combination with a drug or active agent if that drug or active agent is not compromised by the conditions of the sintering process.

The ability to increase the amount of expansion in either sintered or unsintered expandable polymers has a wide variety of applications in medical, industrial, and consumer products. For example: laminate structures with varying properties for filters and membranes; medical implants with tailored porosities to control body fluid leakage and tissue ingrowth; radially expandable PTFE with reduced expansion force and/or increased expansion ratios for endovascular applications.

A variety of forms and sizes are included in the scope of the invention. For example, flat sheets, hollow tubes, and solid rods, can be manufactured and utilized in many applications. Furthermore, the invention is applicable to any structures formable by conventional expandable polymer methods.

Expanded PTFE material is characterized by lengthwise-oriented fibrils interrupted by transverse nodes. The pore size in microns is typically determined by measuring fiber length between the nodes (internodal distance). To compute fibril length, the material is viewed under sufficient magnification. A fibril length is measured from one edge of one node to the edge of an adjacent node. Fibril lengths are measured from the sample to compute a mean fibril length.

Nodes and fibrils may be further characterized by their relative geometry. That is, nodes by length, width, and height; and fibrils, by diameter and length. It is the relative geometry of nodes to fibrils, as well as, internodal distance and fibril density that determines porosity and permeability of porous PTFE. The physical space between connecting nodes is composed of solid thread like PTFE fibers called fibrils in conjunction with a void volume. Fibril density refers to the relative volume consumed by fibrils between the nodes.

Permeability or hydraulic conductivity is related to material porosity. Permeability to fluid flow can be determined by measuring the amount of pressure required for water to permeate the pores of the material. Water entry pressure (WEP) is a good measuring technique to assess this trait because it closely mimics the permeation process at the liquid/solid interface. WEP is defined as the pressure value necessary to push water into the pores of a synthetic tubular substrate and can be classified as: High (>400 mm Hg), Medium (200–400 mm Hg), and Low (<200 mm Hg). To compute WEP, the material is subjected to an incrementally increasing water pressure until small beads of water appear on the surface.

Machine direction (MD) refers to the direction in which the polymeric material travels through the processing machine. Transverse direction (TD) refers to the direction that is perpendicular to the MD. Longitudinal Tensile Strength (LTS) is measured in pounds per square inch by dividing the tensile force applied to the material by the cross-sectional area of the material. Radial Tensile Strength (RTS) is also measured in pounds per square inch. RTS is obtained by dividing the radial expansion force applied to the material by the cross-sectional area of the material. Cross-sectional area is the amount of material subjected to a controlled strain during tensile testing defined as the sample width multiplied by its thickness.

Suture Retention strength (SRT), measured in pounds, indicates the amount of force needed to pull out sutures from the polymeric material.

The invention will now be described with reference to exemplary embodiments. Cylinders, tubes, sheets, or other shapes can be created by either of these embodiments.

The embodiments involve the use of expandable polymers. Although expandable polymer material may be prepared in a variety of ways, one method involves the use of wettable liquid to aid an initial extrusion process. A wettable liquid is capable of entering the pores of the expandable polymer resin. The invention is not limited to expandable polymers prepared by extrusion, or by the use of a wettable liquid for extrusion.

By way of example, an expandable polymer resin, such as PTFE resin (Fluon CD-123 obtained from ICI Americas), may be blended with a first wettable liquid, such as ISOPAR-H odorless solvent (produced by EXXON Corporation), to form a lubricated powder. The wettable liquid can further include one or more drugs or agents desired to be incorporated into the expandable polymer. This results in the lubricated powder containing the one or more drugs or agents.

The wettable liquid may be mixed with the resin to control the degree of material shear that occurs during subsequent extrusion and to prevent excessive shear, which can damage the material. Again, the wettable liquid can include one or more drugs or agents for incorporation into the expandable polymer. By application of pressure, the lubricated powder may then be preformed into a billet, typically shaped like a large cylinder.

Alternatively, the resin may be mixed with a powder form of the one or more drugs or agents. The combination of the resin with the powder can occur before, during, or after the addition of the wettable liquid in forming the expandable polymer.

Using a ram-type extruder, the billet may be extruded through a die having a desired cross-section, typically a circle, thereby forming a cylinder. A variety of shapes may be formed by extrusion, such as a solid or hollow cylinder, a flat sheet, a rectangle and the like.

FIG. 1 depicts a flowchart illustrating a first embodiment method for forming an extruded polymer for use in making an expanded polymer in accordance with the present invention. A polymer resin is mixed with a first wettable liquid and at least one drug or agent to form a mixture (step 100). It should be noted that in this, and other embodiments, the polymer resin can be formed by mixing a powder formed at least partially of a drug or an agent to form the polymer resin. The mixture is formed into a pre-form (step 102). The pre-form is then extruded to form an extruded polymer (step 104). The first wettable liquid can be in the form of a solvent, such as ISOPAR-H odorless solvent (produced by EXXON Corporation), to form a lubricated powder. Other liquids that can form the first wettable liquid can include Polyethylene Glycol (PEG), Water Soluble Polymers (Polyvinyl Alcohol, Gelatins, HEMA, Polyvinyl Pyrollidone, Alginates, SAIB), Low Molecular Weight Polymers (polylactic acid, polycaprolactone), Plasticizers (citrate esters), Oils/Waxes/Fats (fish oil, mineral oil, vegetable oil, paraffin, beeswax, omega 3 fatty acids), Solvents (n-Methyl Pyrollidone, alcohol, Dimethylsulfoxide), Biodegradable polymers, Surfactants (tween, polysorbate), and an aqueous dispersion. The at least one drug or agent can be a number of different materials or substances, including but not limited to those found in Table 1 of this description. The inclusion of the drug or agent at the mixing stage of the polymer resin provides for a resulting expanded polymer with the drug or agent well established therein and able to emit to affect a target location within a patient body.

Figure 2:
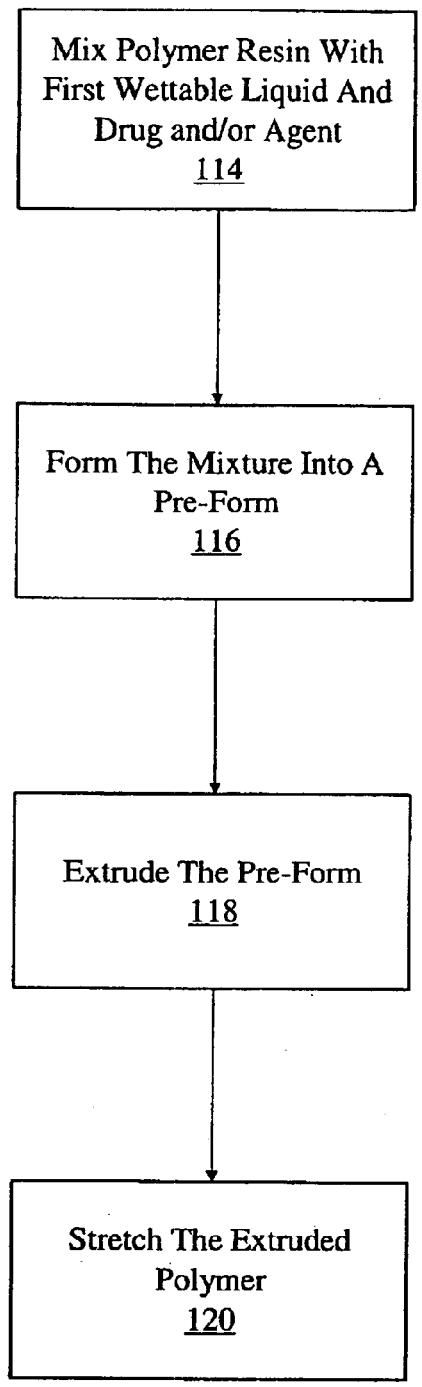
FIG. 2 is a flowchart illustrating another example method for forming an article according to one aspect of the present invention.

FIG. 2 depicts a flowchart illustrating an additional step to the method shown in FIG. 1. A polymer resin is mixed with a first wettable liquid and at least one drug or agent to form a mixture (step 114). The mixture is formed into a pre-form (step 116). The pre-form is then extruded to form an extruded polymer (step 118). Then the extruded polymer is stretched to form a stretched polymer (step 120).

Figure 3:
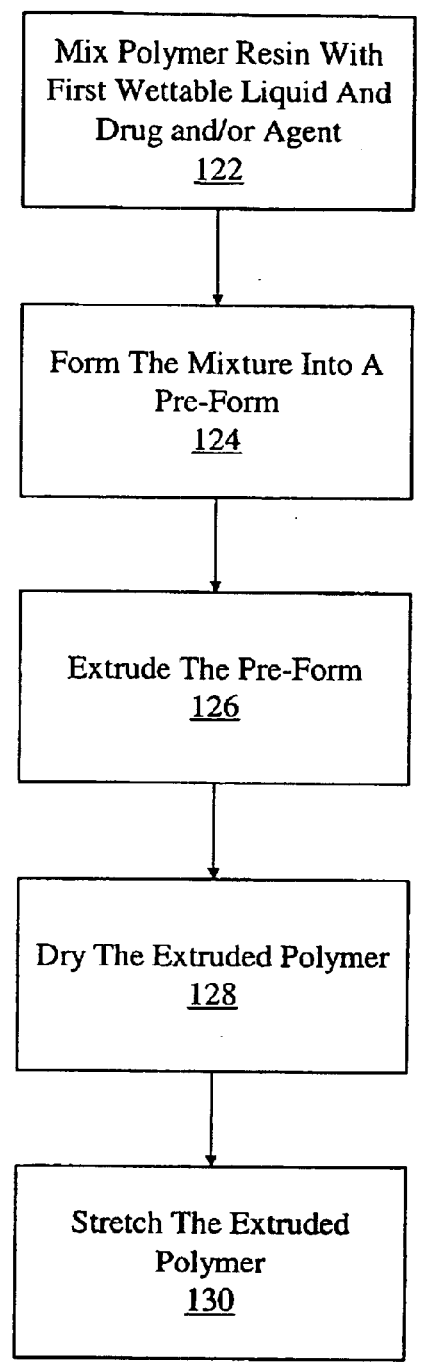
FIG. 3 is a flowchart illustrating another example method for forming an article according to one aspect of the present invention.

FIG. 3 depicts a flowchart illustrating an additional step to the method shown in FIG. 2. A polymer resin is mixed with the first wettable liquid and at least one drug or agent to form a mixture (step 122). The mixture is formed into a pre-form (step 124). The pre-form is then extruded to form an extruded polymer (step 126). The extruded polymer is dried (step 128). After drying, the extruded polymer is stretched to form a stretched or expanded polymer (step 130).

Figure 4:
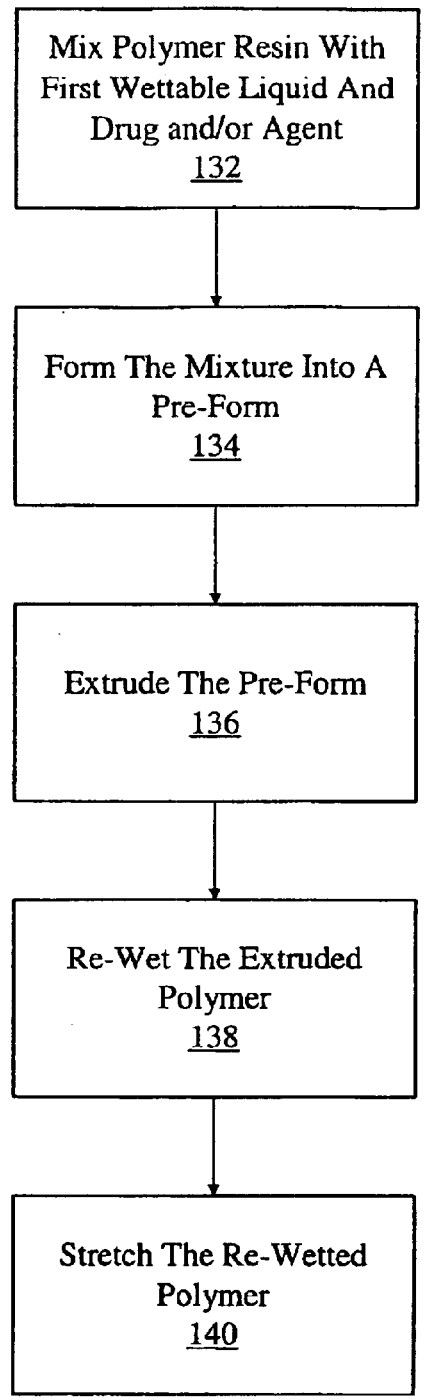
FIG. 4 is a flowchart illustrating another example method for forming an article according to one aspect of the present invention.

FIG. 4 depicts still another flowchart illustrating a method for forming an expanded polymer utilizing a re-wetting process. A polymer resin is mixed with the first wettable liquid and at least one drug or agent to form a mixture (step 132). The mixture is formed into a pre-form (step 134). The pre-form is then extruded to form an extruded polymer (step 136). The extruded polymer is re-wetted with either a similar or same liquid to the first wettable liquid, or alternatively with a second wettable liquid (step 138). After re-wetting, the re-wetted extruded polymer is stretched to form a stretched or expanded polymer (step 140).

Figure 5:
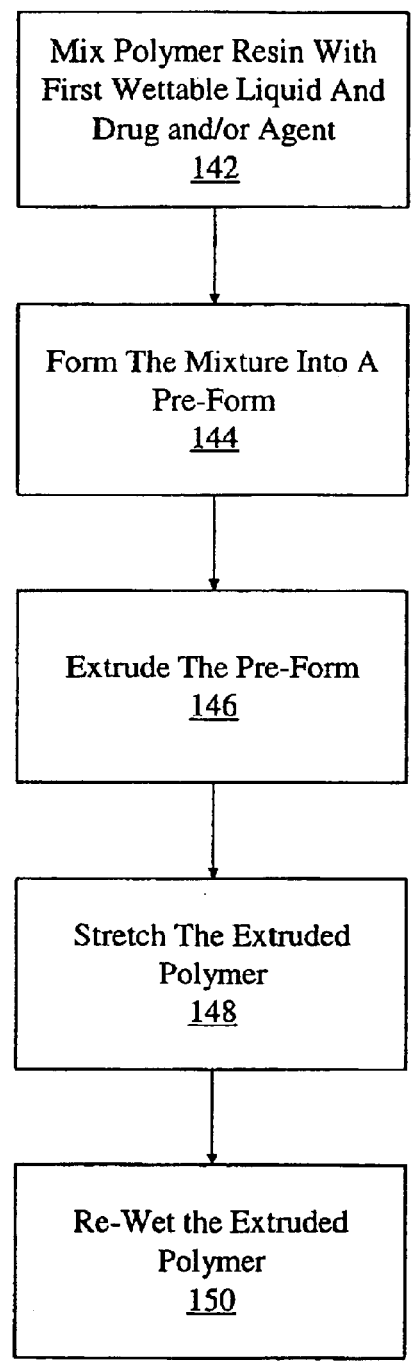
FIG. 5 is a flowchart illustrating another example method for forming an article according to one aspect of the present invention.

FIG. 5 depicts another flowchart illustrating a method for forming an expanded polymer utilizing a re-wetting process that is similar to that of FIG. 4, but in a different order. A polymer resin is mixed with the first wettable liquid and at least one drug or agent to form a mixture (step 142). The mixture is formed into a pre-form (step 144). The pre-form is then extruded to form an extruded polymer (step 146). Instead of re-wetting at this point, the extruded polymer is stretched (step 148). The stretched extruded polymer is then re-wetted with either a similar or same liquid to the first wettable liquid, or alternatively with a second wettable liquid (step 150) to form a stretched or expanded polymer.

Figure 6:
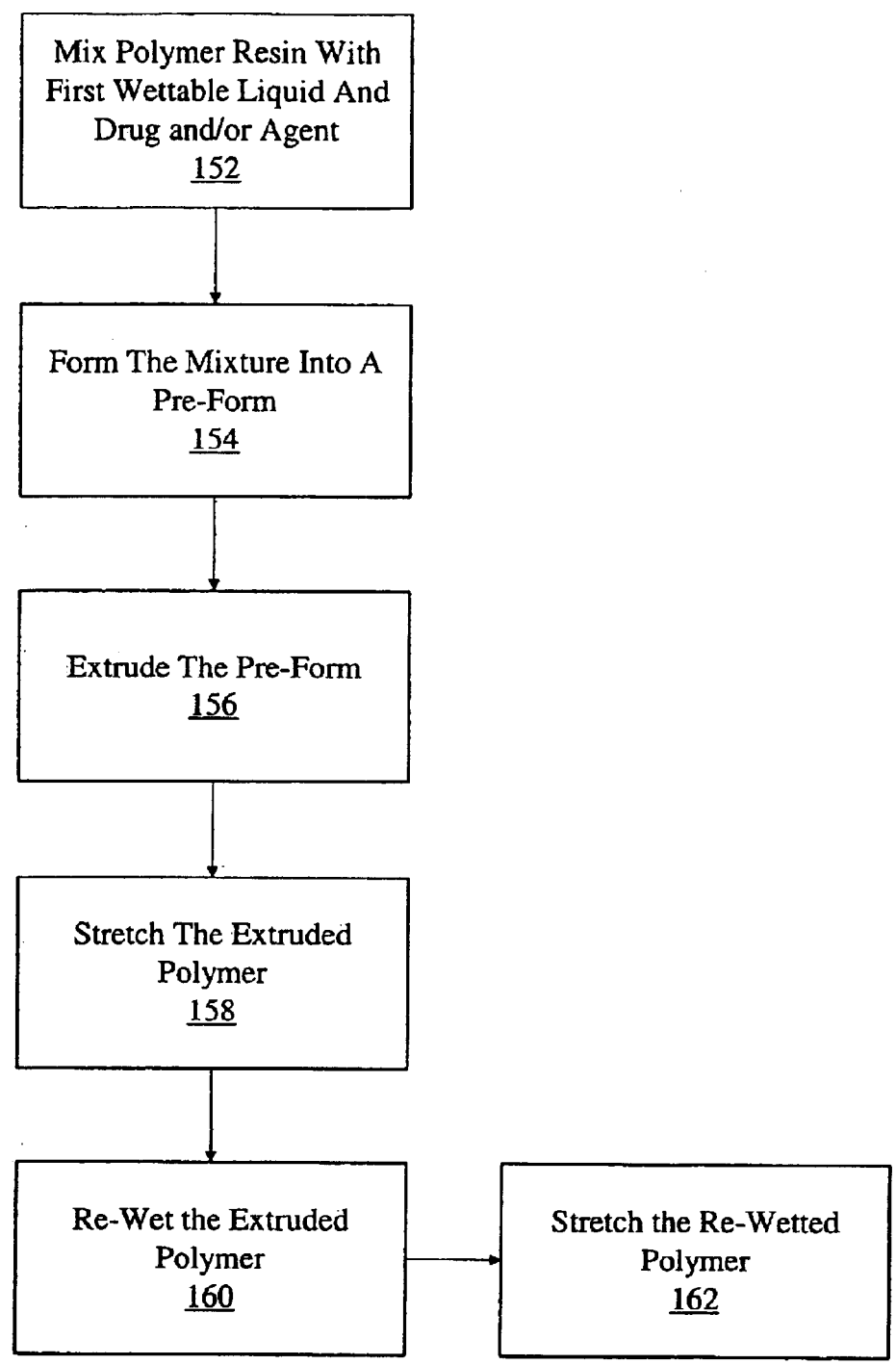
FIG. 6 is a flowchart illustrating another example method for forming an article according to one aspect of the present invention.

FIG. 6 depicts another flowchart illustrating a method for forming an expanded polymer utilizing a re-wetting process similar to that of FIG. 5, but with an extra stretching step. A polymer resin is mixed with the first wettable liquid and at least one drug or agent to form a mixture (step 152). The mixture is formed into a pre-form (step 154). The pre-form is then extruded to form an extruded polymer (step 156). The extruded polymer is stretched (step 158). The stretched extruded polymer is then re-wetted with either a similar or same liquid to the first wettable liquid, or alternatively with a second wettable liquid (step 160). The re-wetted stretched expanded polymer is then stretched again to form a stretched or expanded polymer (step 162).

Figure 7:
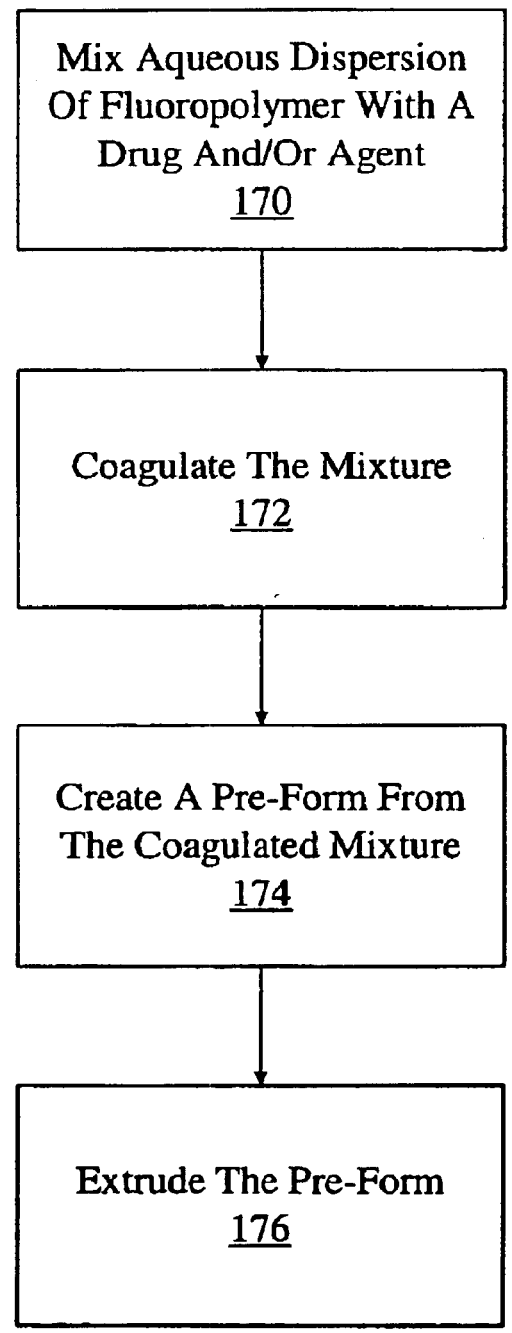
FIG. 7 is a flowchart illustrating another example method for forming an article according to one embodiment of the present invention.

The process for creating the expanded polymer can also be modified to include the use of an aqueous dispersion of fluoropolymer, such as for example, PTFE or PET, with a drug or agent mixed therein. For example, FIG. 7 shows a flow chart illustrating such a method. An aqueous dispersion of fluoropolymer is mixed together with at least one of a drug or agent to form a mixture (step 170). The mixture is coagulated (step 172). A pre-form is then created from the coagulated mixture (step 174). Similar to the above methods, the pre-form is then extruded (step 176) to form an extruded polymer with the drug or agent inter-mixed.

Figure 8:
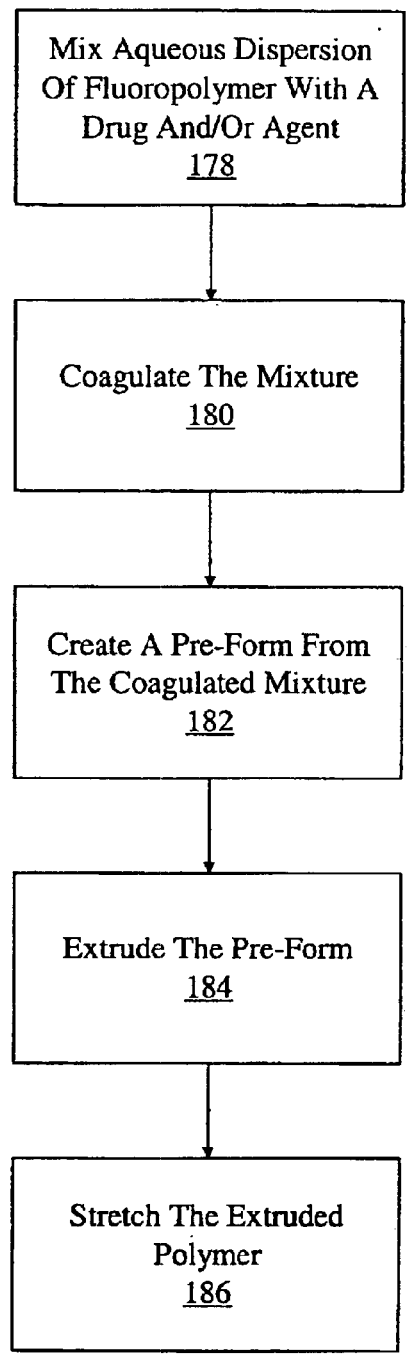
FIG. 8 is a flowchart illustrating another example method for forming an article according to one aspect of the present invention.

FIG. 8 shows a method similar to that of FIG. 2. An aqueous dispersion of fluoropolymer is mixed together with at least one of a drug or agent to form a mixture (step 178). The mixture is coagulated (step 180). A pre-form is then created from the coagulated mixture (step 182). The pre-form is then extruded (step 184) to form an extruded polymer with the drug or agent inter-mixed. The extruded polymer is then stretched to form the expanded polymer (step 186).

Figure 9:
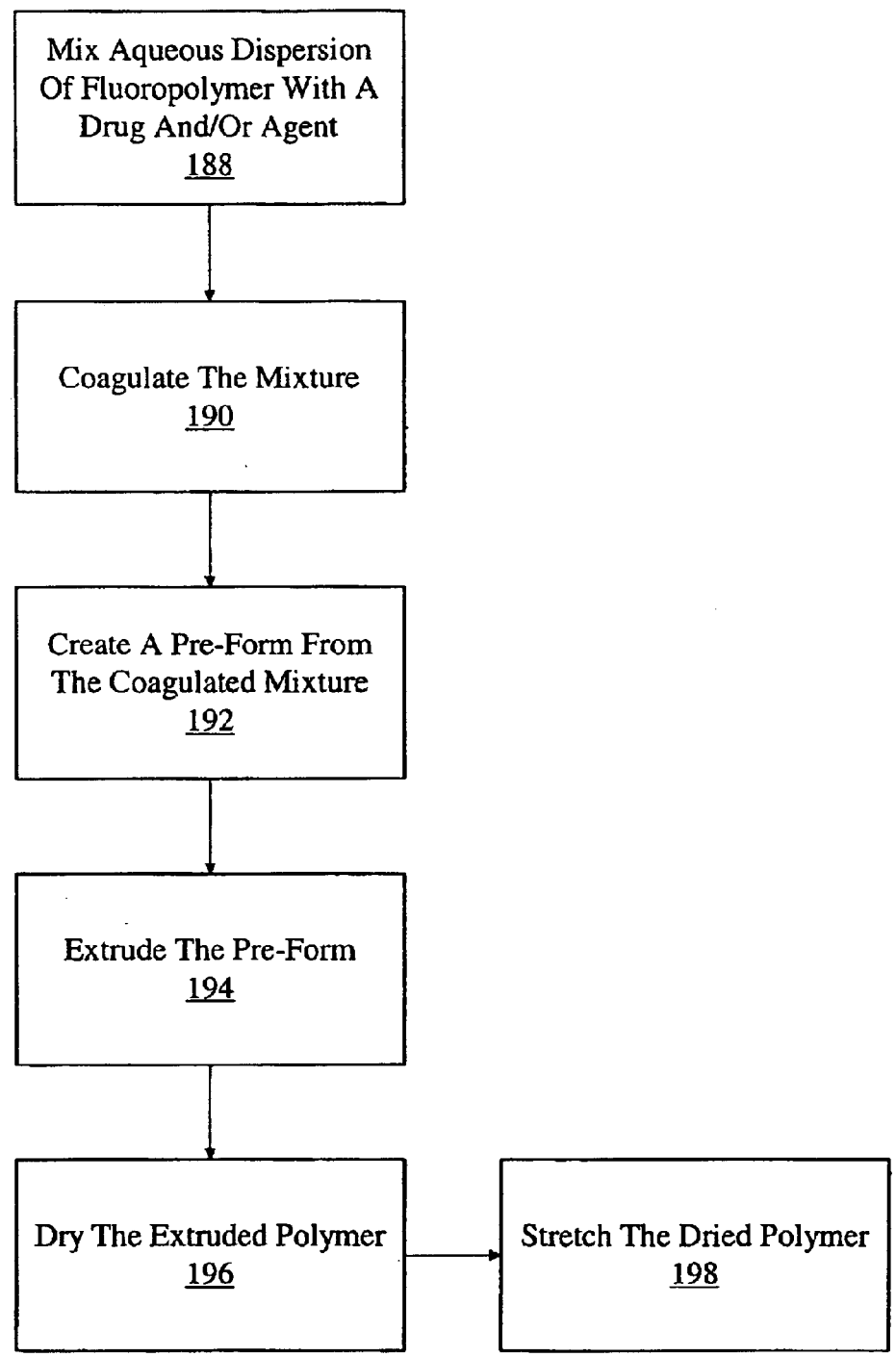
FIG. 9 is a flowchart illustrating another example method for forming an article according to one aspect of the present invention.

FIG. 9 shows a method similar to that of FIG. 3. An aqueous dispersion of fluoropolymer is mixed together with at least one of a drug or agent to form a mixture (step 188). The mixture is coagulated (step 190). A pre-form is then created from the coagulated mixture (step 192). The pre-form is then extruded (step 194) to form an extruded polymer with the drug or agent inter-mixed. The extruded polymer is dried (step 196). The dried extruded polymer is then stretched to form the expanded polymer (step 198).

Figure 10:
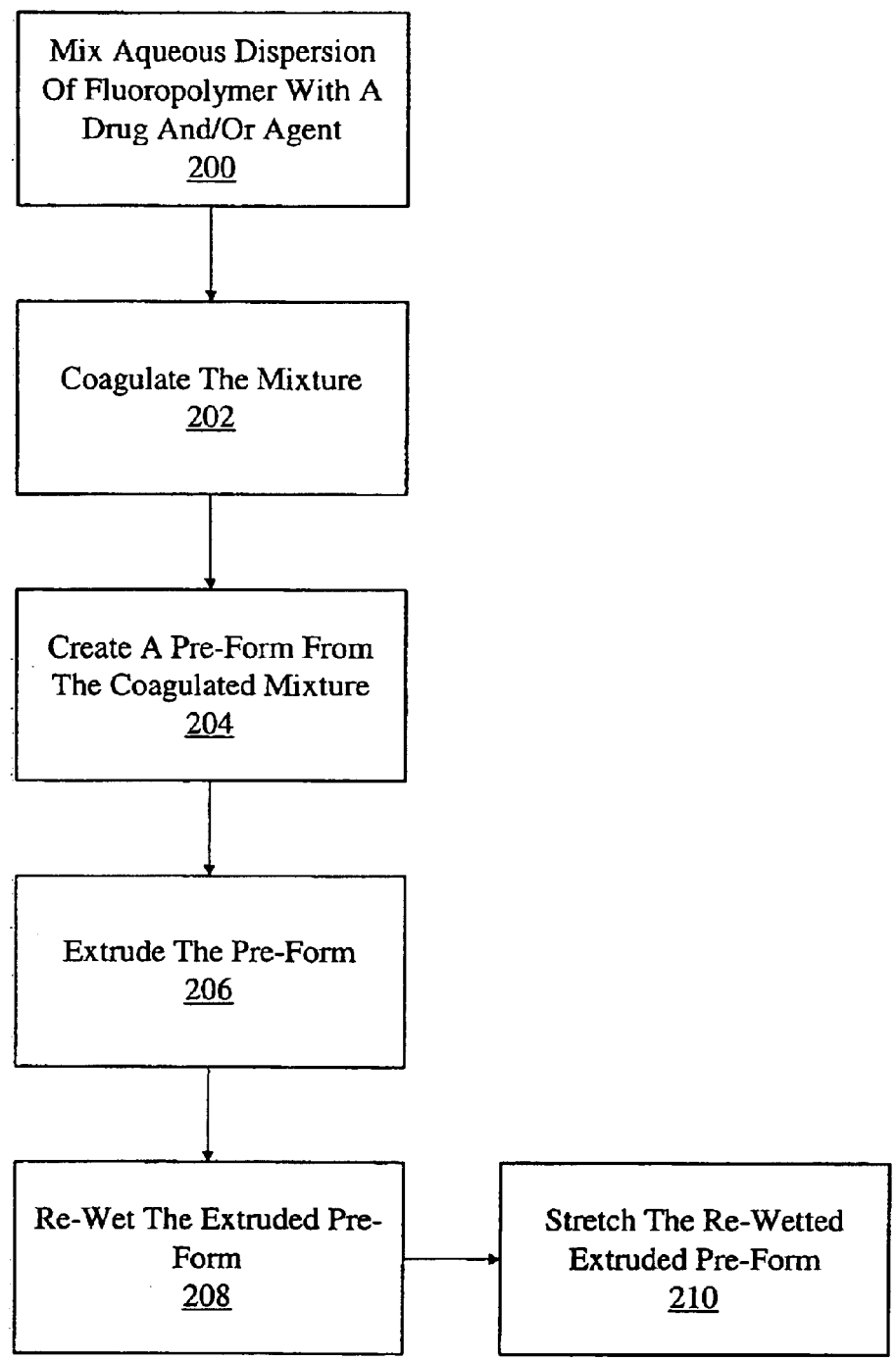
FIG. 10 is a flowchart illustrating another example method for forming an article according to one aspect of the present invention.

FIG. 10 shows a method similar to that of FIG. 4. An aqueous dispersion of fluoropolymer is mixed together with at least one of a drug or agent to form a mixture (step 200). The mixture is coagulated (step 202). A pre-form is then created from the coagulated mixture (step 204). The pre-form is then extruded (step 206) to form an extruded polymer with the drug or agent inter-mixed. The extruded polymer is re-wetted with either a similar or same liquid to the first wettable liquid, or alternatively with a second wettable liquid (step 208). After re-wetting, the re-wetted extruded polymer is stretched to form a stretched or expanded polymer (step 210).

Figure 11:
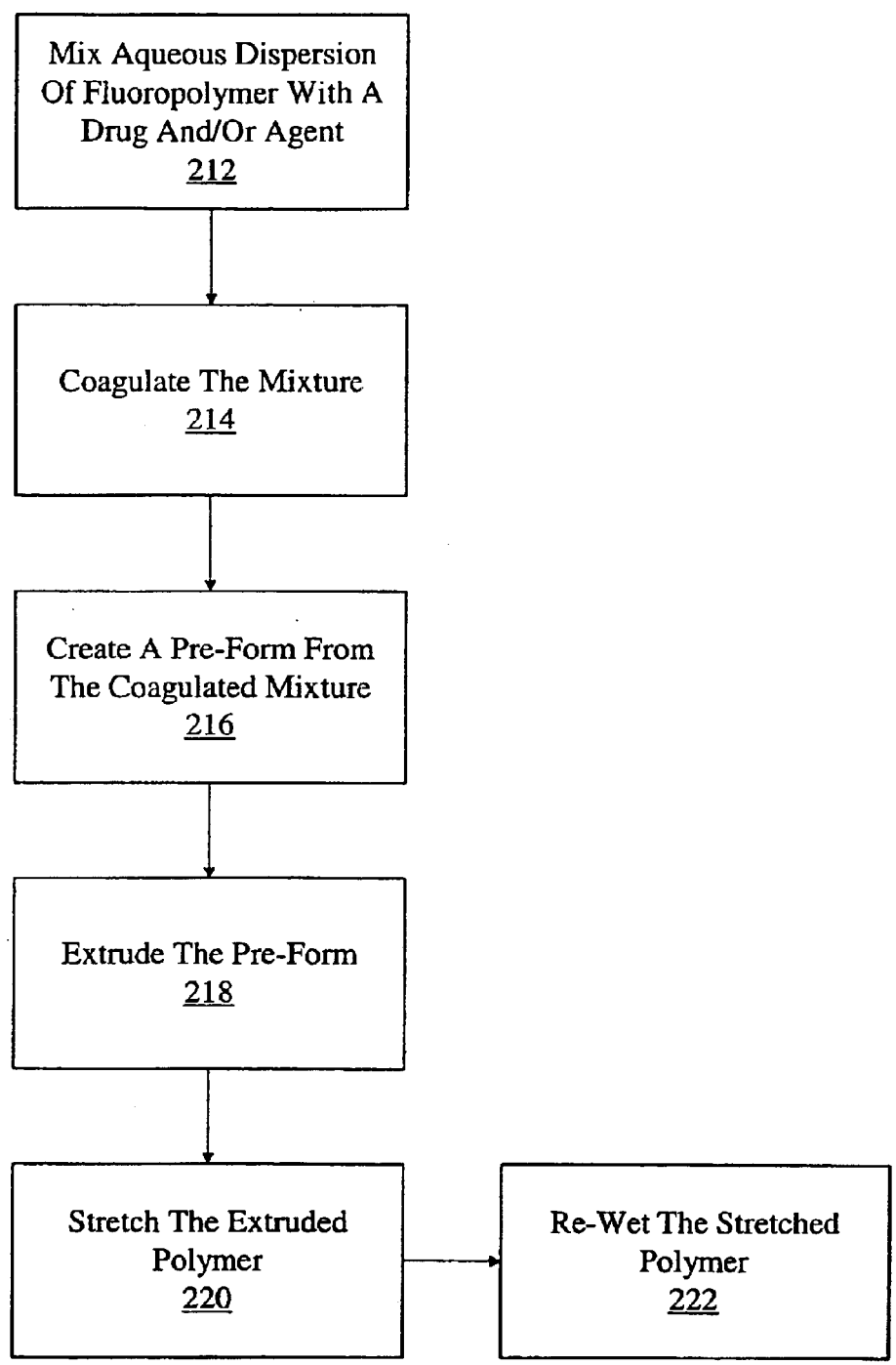
FIG. 11 is a flowchart illustrating another example method for forming an article according to one aspect of the present invention.

FIG. 11 shows a method similar to that of FIG. 5. An aqueous dispersion of fluoropolymer is mixed together with at least one of a drug or agent to form a mixture (step 212). The mixture is coagulated (step 214). A pre-form is then created from the coagulated mixture (step 216). The pre-form is then extruded (step 218) to form an extruded polymer with the drug or agent inter-mixed. The extruded polymer is then stretched (step 220). The stretched extruded polymer is re-wetted with either a similar or same liquid to the first wettable liquid, or alternatively with a second wettable liquid (step 222).

Figure 12:
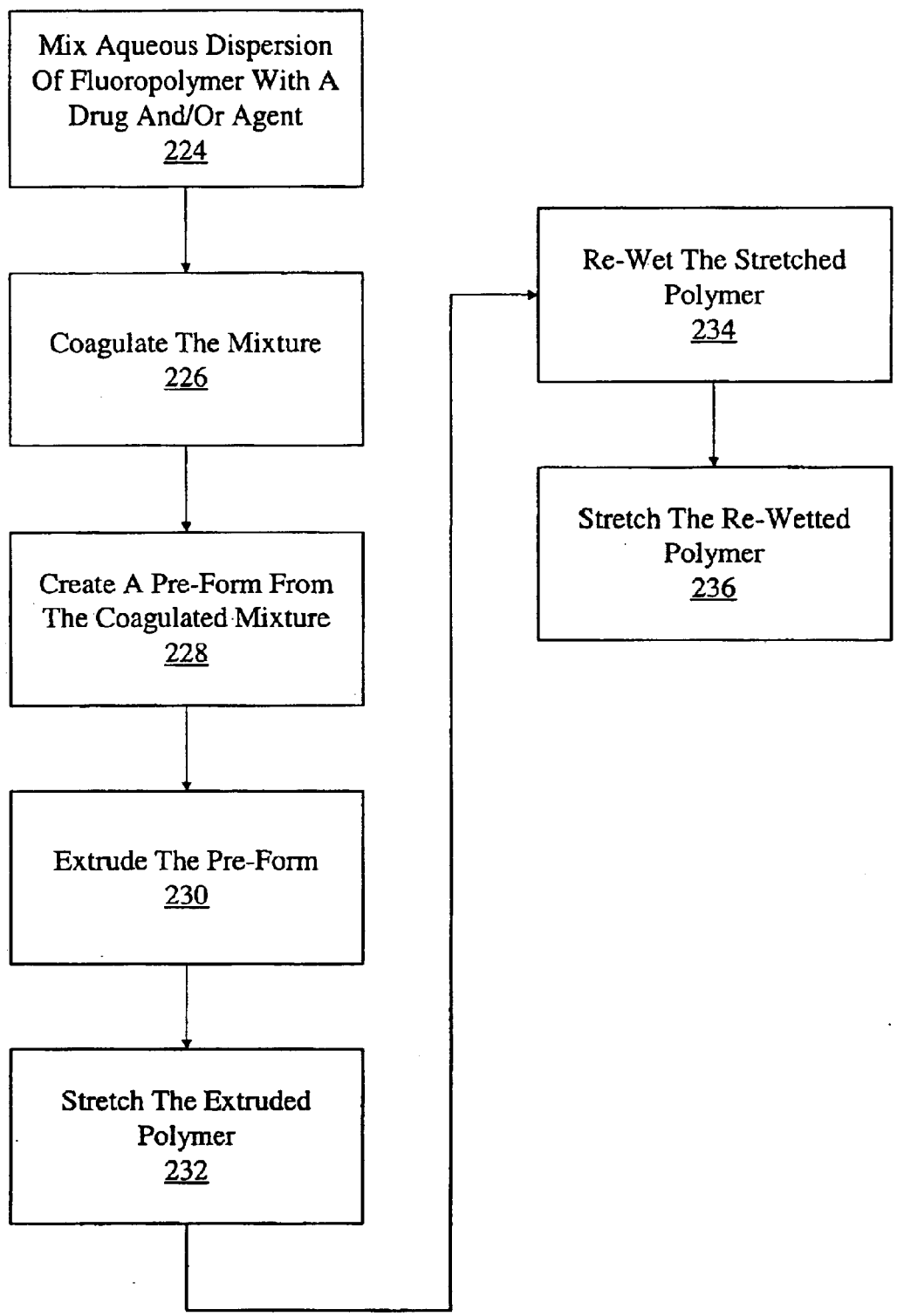
FIG. 12 is a flowchart illustrating another example method for forming an article according to one aspect of the present invention.

FIG. 12 depicts a method similar to that of FIG. 6. An aqueous dispersion of fluoropolymer is mixed together with at least one of a drug or agent to form a mixture (step 224).

The mixture is coagulated (step 226). A pre-form is then created from the coagulated mixture (step 228). The pre-form is then extruded (step 230) to form an extruded polymer with the drug or agent inter-mixed. The extruded polymer is stretched (step 232). The stretched extruded polymer is re-wetted with either a similar or same liquid to the first wettable liquid, or alternatively with a second wettable liquid (step 234). After re-wetting, the re-wetted stretched extruded polymer is again stretched to form a stretched or expanded polymer (step 236).

Figure 13:
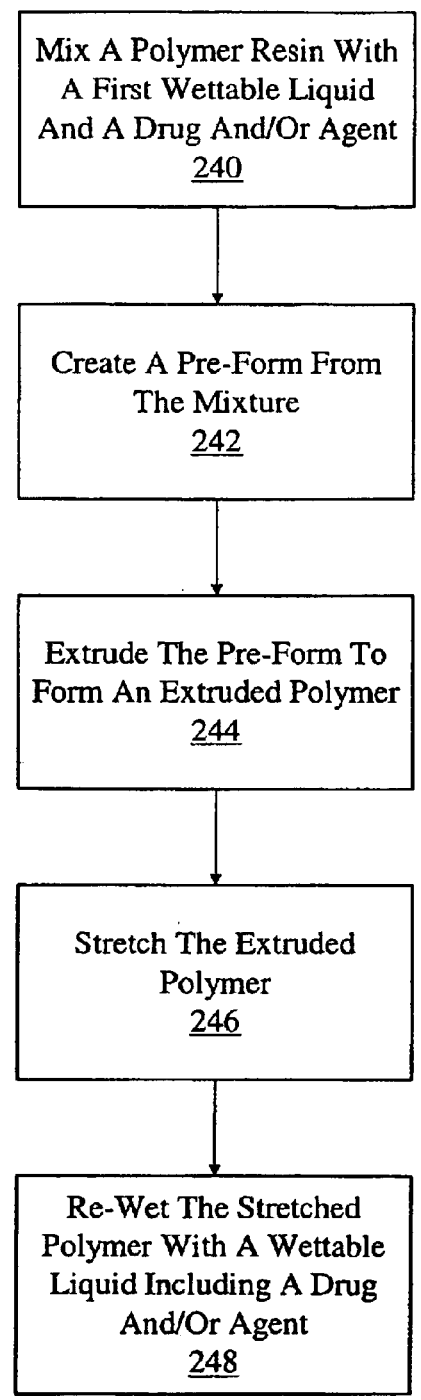
FIG. 13 is a flowchart illustrating another example method for forming an article according to one embodiment of the present invention.

In accordance with another embodiment of the present invention, a method of forming an expanded polymer is shown in FIG. 13. A polymer resin is mixed with a first wettable liquid and at least one of a drug or an agent to form a mixture (step 240). The mixture is formed into a pre-form (step 242). The pre-form is extruded to form an extruded polymer (step 244). The extruded polymer is then stretched (step 246). The stretched extruded polymer is then re-wet with a second wettable liquid that is either the same or similar to the first wettable liquid, or of a different composition, and includes at least one of a drug or agent (step 248).

Figure 14:
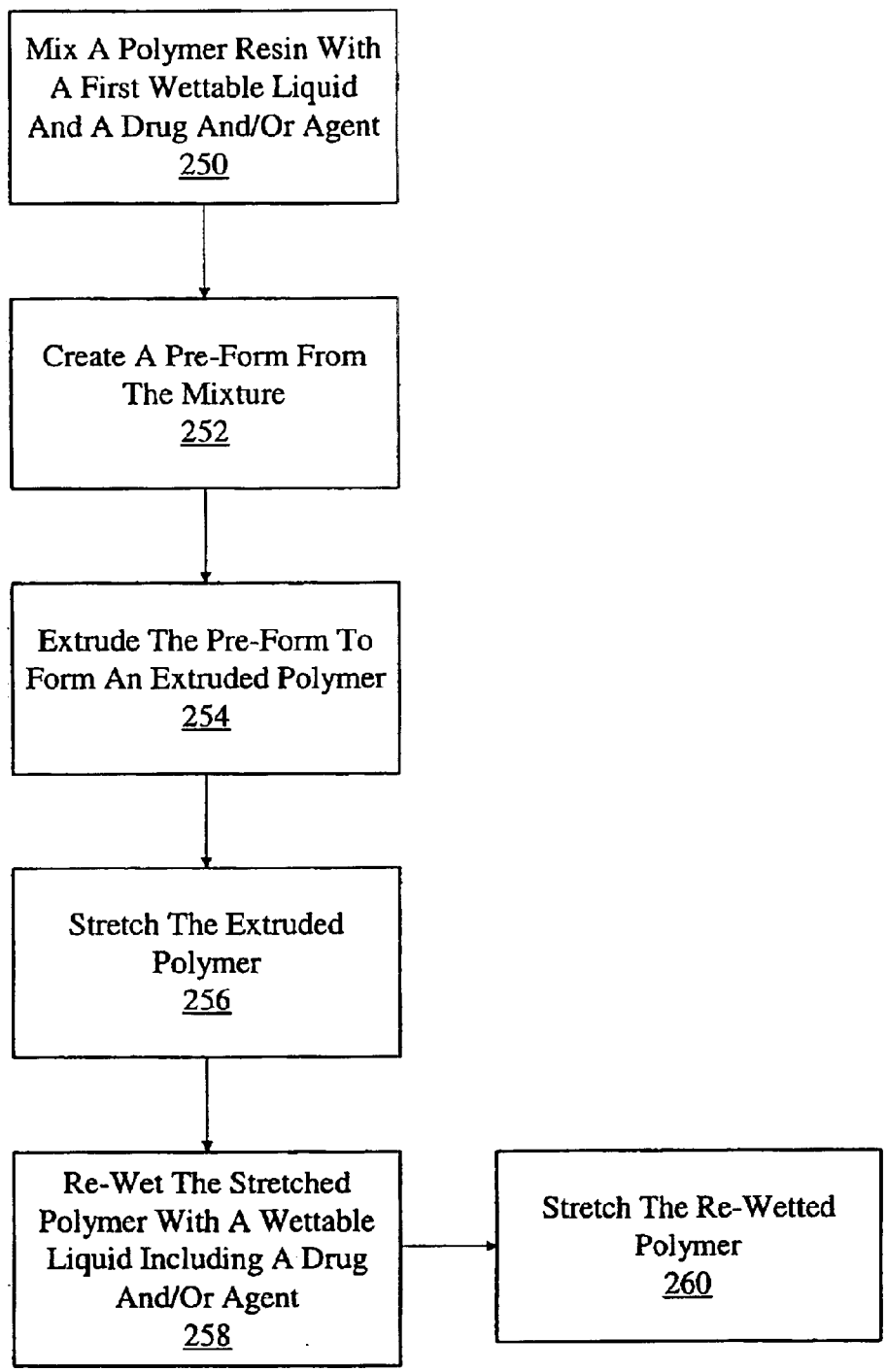
FIG. 14 is a flowchart illustrating another example method for forming an article according to one aspect of the present invention.

FIG. 14 depicts another method of forming an expanded polymer according to one aspect of the present invention. A polymer resin is mixed with a first wettable liquid and at least one of a drug or an agent to form a mixture (step 250). The mixture is formed into a pre-form (step 252). The pre-form is extruded to form an extruded polymer (step 254). The extruded polymer is then stretched (step 256). The stretched extruded polymer is then re-wet with a second wettable liquid that is either the same or similar to the first wettable liquid, or of a different composition, and includes at least one of a drug or agent (step 258). Finally, the re-wetted stretched polymer is again stretched to form the expanded polymer (step 260).

Figure 15:
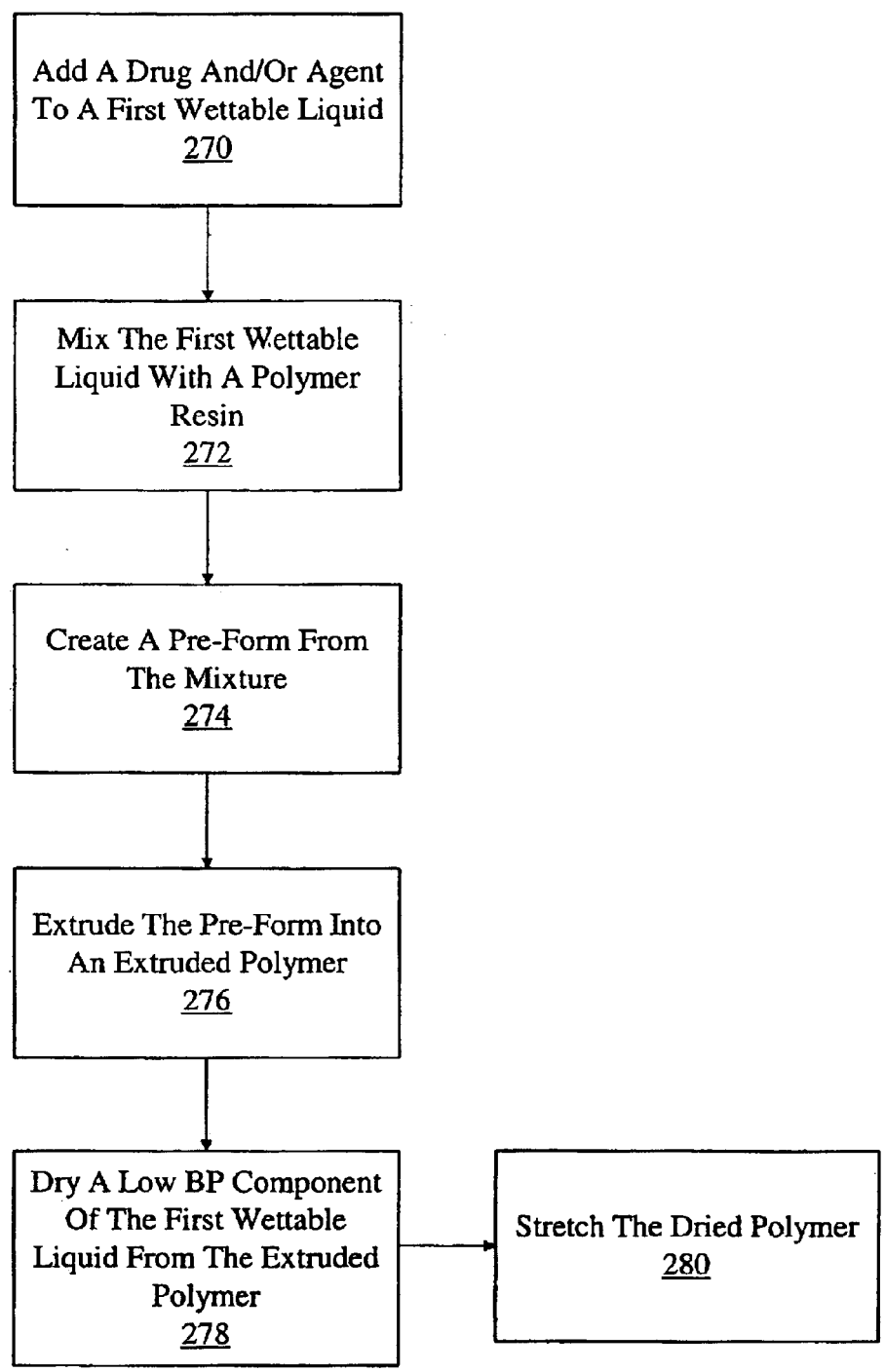
FIG. 15 is a flowchart illustrating another example method for forming an article according to one embodiment of the present invention.

In accordance with another embodiment of the present invention, FIG. 15 depicts another method for forming an expanded polymer. At least one of a drug or agent is combined with a first wettable liquid (step 270). The first wettable liquid is mixed with a polymer resin to form a mixture (step 272). The mixture is formed into a pre-form (step 274). The pre-form is then extruded to form an extruded polymer (step 276). A low BP component of the first wettable liquid is dried from the extruded polymer (step 278). The dried extruded polymer is then stretched to form the expanded polymer (step 280).

Figure 16:
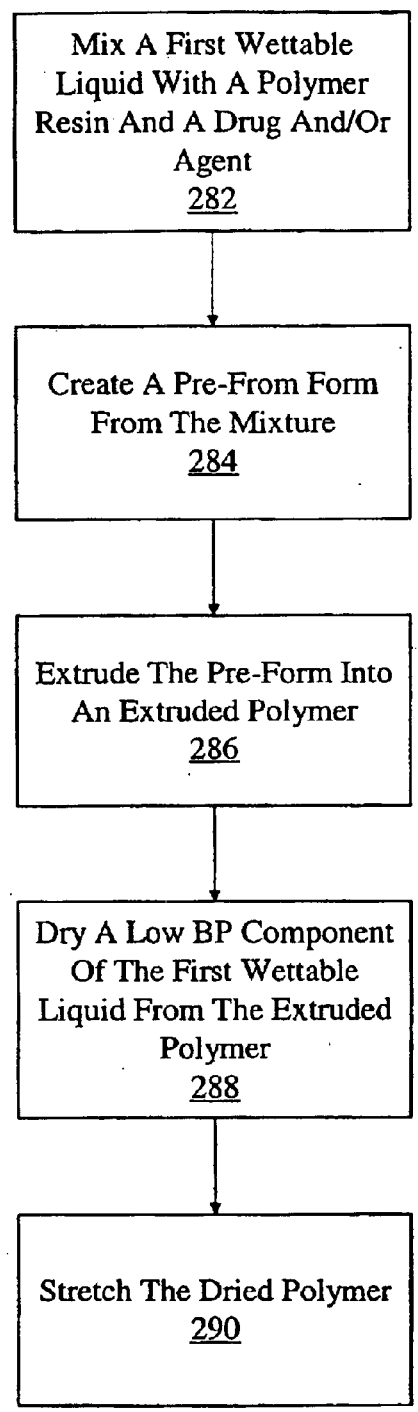
FIG. 16 is a flowchart illustrating another example method for forming an article according to one aspect of the present invention.

FIG. 16 depicts another method for forming an expanded polymer in accordance with another embodiment of the present invention. A first wettable liquid is mixed with a polymer resin and at least one of a drug or agent to form a mixture (step 282). The mixture is formed into a pre-form (step 284). The pre-form is then extruded to form an extruded polymer (step 286). A low BP component of the first wettable liquid is dried from the extruded polymer (step 288). The dried extruded polymer is then stretched to form the expanded polymer (step 290).

Figure 17:
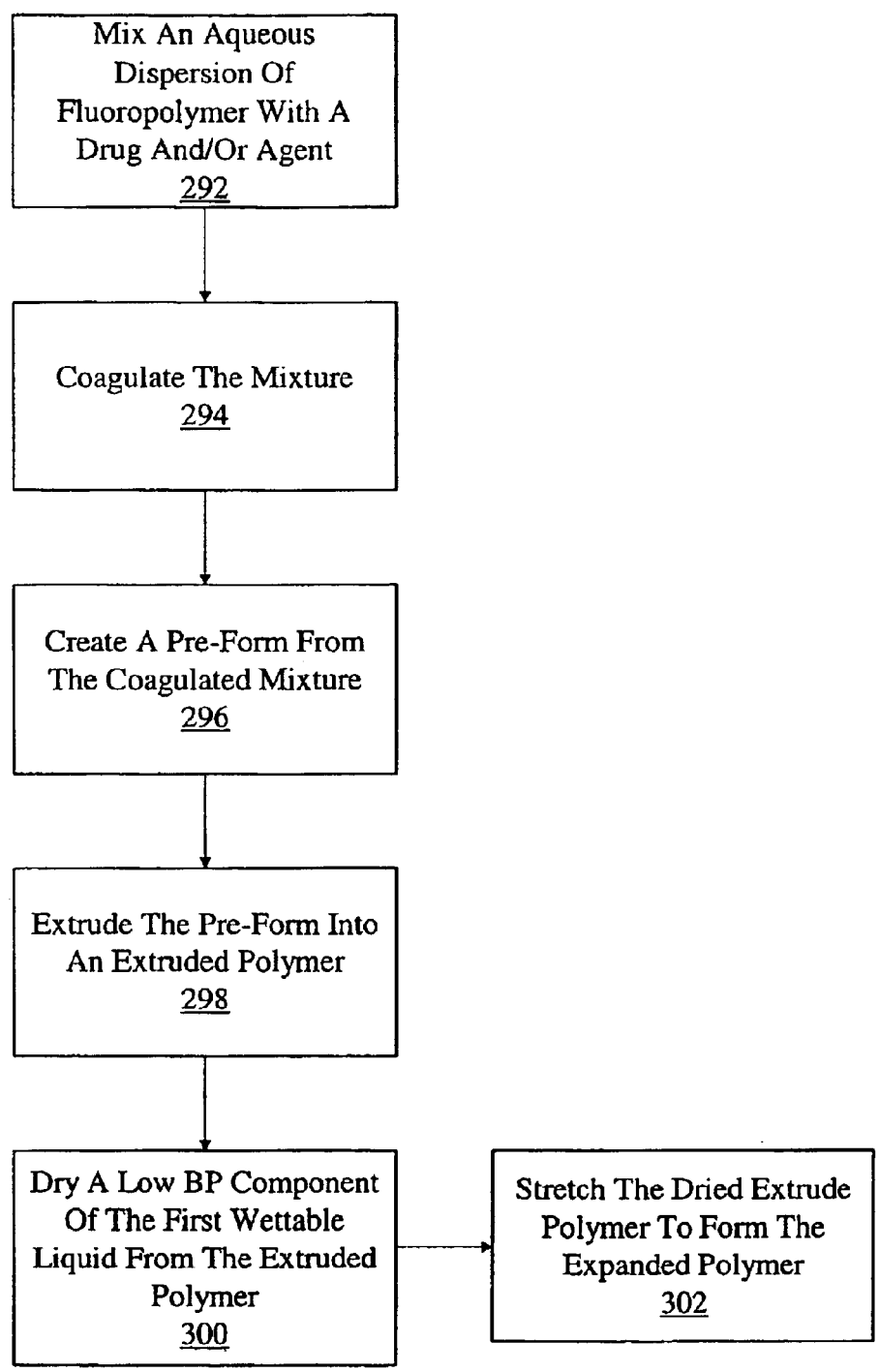
FIG. 17 is a flowchart illustrating another example method for forming an article according to one aspect of the present invention.

FIG. 17 depicts yet another method for forming an expanded polymer in accordance with one embodiment of the present invention. An aqueous dispersion of fluoropolymer is mixed with at least one of a drug or agent to form a mixture (step 292). The mixture is coagulated (step 294). The coagulated mixture is then formed into a pre-form (step 296). The pre-form is then extruded to form an extruded polymer (step 298). A low BP component of the first wettable liquid is dried from the extruded polymer (step 300). The dried extruded polymer is then stretched to form the expanded polymer (step 302).

Figure 18:
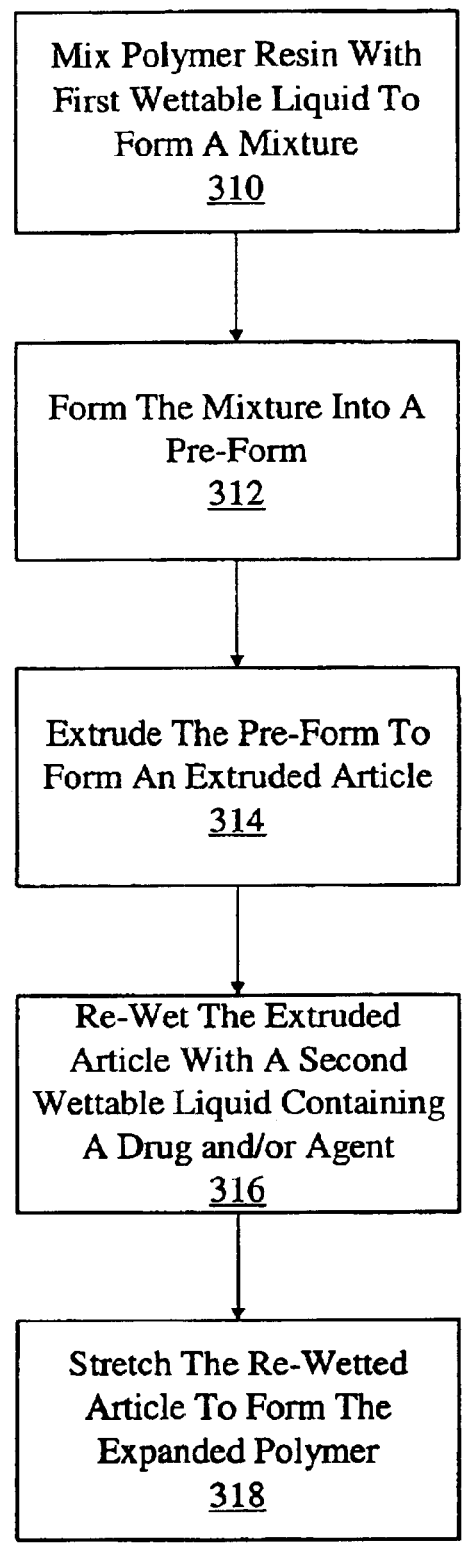
FIG. 18 is a flowchart illustrating another example method for forming an article according to one aspect of the present invention.

FIG. 18 depicts a method for forming an expanded polymer in accordance with one embodiment of the present invention. A polymer resin is mixed with a first wettable liquid to form a mixture (step 310). A pre-form is formed from the mixture (step 312). The pre-form is extruded to form an extruded article (step 314). The extruded article is re-wetted with the first wettable liquid and/or a second wettable liquid (step 316). In this embodiment, the second wettable liquid is at least partially formed with a drug and/or an agent. The re-wetted article is stretched to form the expanded polymer article (step 318).

Figure 19:
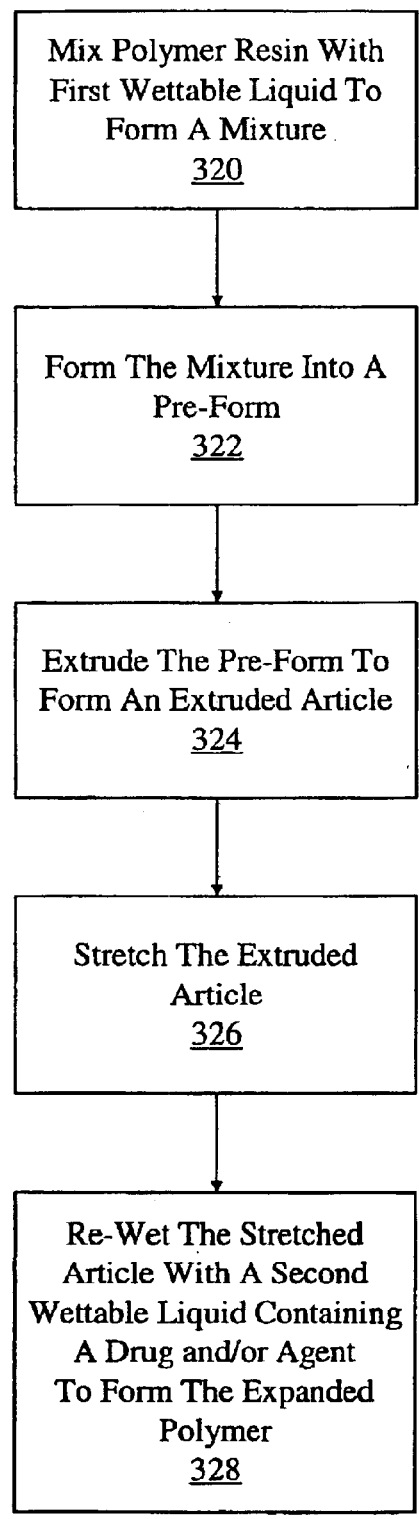
FIG. 19 is a flowchart illustrating another example method for forming an article according to one aspect of the present invention.

FIG. 19 depicts a method for forming an expanded polymer in accordance with another embodiment of the present invention. A polymer resin is mixed with a first wettable liquid to form a mixture (step 320). A pre-form is formed from the mixture (step 322). The pre-form is extruded to form an extruded article (step 324). The extruded article is stretched (step 326). The extruded article is re-wetted with a second wettable liquid to form the expanded polymer (step 328). In this embodiment, the second wettable liquid is formed at least partially with a drug and/or an agent.

Figure 20:
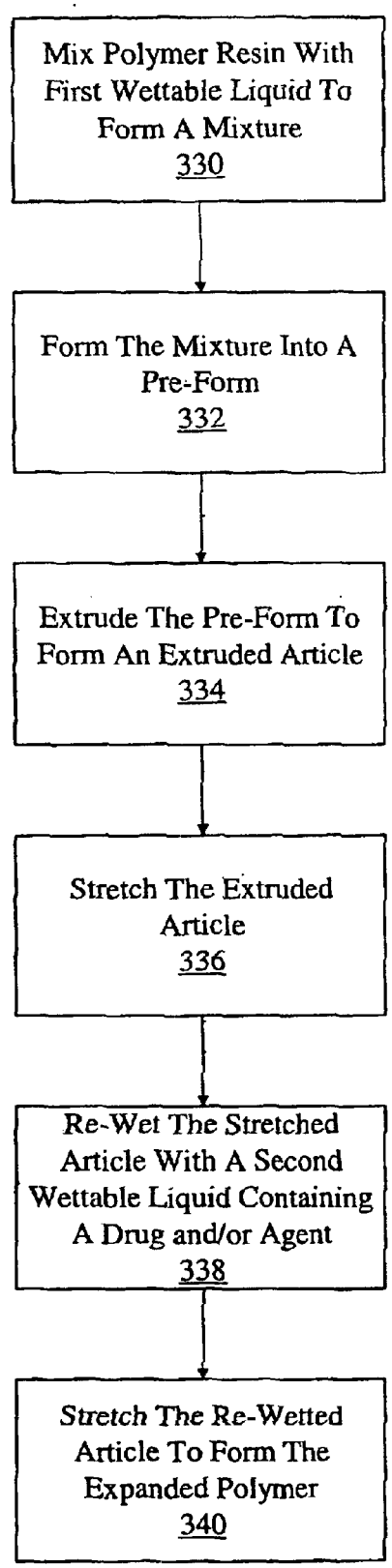
FIG. 20 is a flowchart illustrating another example method for forming an article according to one aspect of the present invention.

FIG. 20 depicts a method for forming an expanded polymer in accordance with another embodiment of the present invention. A polymer resin is mixed with a first wettable liquid to form a mixture (step 330). A pre-form is formed from the mixture (step 332). The pre-form is extruded to form an extruded article (step 334). The extruded article is stretched (step 336). The extruded article is re-wetted with a second wettable liquid (step 338). In this embodiment, the second wettable liquid is formed at least partially with a drug and/or an agent. The re-wetted extruded article is stretched to form the expanded polymer article (step 340).

With regard to the embodiments described above and shown in FIGS. 18–20, as with the other embodiments described herein, the expanded polymer article can have a number of different shapes, and the drug or agent can be selected from any of those described herein. The first wettable liquid utilized in the method can include a drug and/or agent. Likewise, the polymer resin can be preformed using a powder containing a drug and/or agent.

As described above generally, rewetting involves the application of wettable liquid after completion of activities for which wettable liquid may be used. Removal of any previous wettable liquid is not required before rewetting.

The one or more drugs or agents can be introduced, as discussed, in either of the first and second wettable liquids, or as a powder with the resin, if desired. The one or more drugs or agents can soak in and penetrate the expandable polymer during the manufacturing process.

Use of the second wettable liquid results in substantially uniform material with increased density and substantially altered node structure. Ideally, the second wettable liquid completely saturates the expandable polymer. As with all embodiments described herein, elevated temperature or pressure above ambient conditions may be used in conjunction with the application of a wettable liquid to reduce the time necessary for saturation or aid in saturation of the expandable polymer.

The stretching step is performed preferably at a temperature below a boiling point of the second wettable liquid. Stretching can be performed in more than one direction. Stretching is typically performed, in the case of a cylinder, by applying tensile force to the ends of the cylinder. In the case of a flat sheet, stretching is typically performed in the machine direction. Alternatively, or in addition, stretching may be performed in the radial or transverse direction to a cylinder or flat sheet, respectively. For example, in the case of a hollow cylinder, a mandrel may be used to radially stretch the hollow polymer cylinder. Tensile force may be applied to stretch the cylinder simultaneously with the use of a mandrel or at a different time. Within the scope of the invention, a combination of various stretching may be combined or applied in succession.

As with all embodiments described herein, heat may also be applied to the expandable polymer prior to or during stretching. It is preferable to keep the temperature of the expandable polymer below a boiling point of the second wettable liquid to inhibit loss of the second wettable liquid. It is further preferable to keep the temperature of the expandable polymer and the wettable liquids below a degradation point of any drugs or agents incorporated into the expandable polymer and wettable liquids.

Although ISOPAR-H can be used as the first and second wettable liquids in these embodiments, other permeating liquids are within the scope of the invention and can be considered interchangeable with ISOPAR-H or other wettable liquids. As an example, polyethylene glycol is preferred for in vivo applications because it is a biocompatible liquid. Naphtha is another example of a wettable liquid that may be used within the scope of the invention. Poly lactic acid is a further possible wettable liquid. Alcohol and water may also be used in combination. It is also within the scope of the invention to use one wettable liquid during the initial extrusion process and another wettable liquid for rewetting. Also, the combination of liquids may be used during either extrusion or rewetting.

It should again be noted that the first and second wettable liquids can include the incorporation of drugs and/or agents. The conditions involved in the process of expansion are amenable to such inclusion. This introduces the opportunity to substitute hydrocarbon-based aids, or other extrusion aids, with a plurality of wettable liquids, including alcohol-based and aqueous-based liquids.

One example liquid mentioned as suitable for inclusion in the expanded polymers is polyethylene glycol. The drug or agent, for example Heparin, can mix with the polyethylene glycol to produce the wettable liquid. The expanded polymer resulting from the use of the mixture for the wettable liquid will release Heparin in a controlled manner. Altering the volumes, ratios, and contents of the mixtures can likewise vary the rate of release of the drug or agent. Other drugs or drug agents can be incorporated into the wettable liquid for use in accordance with the teachings of the present invention. Table 1 is provided below of some example drugs or agents suitable for use in accordance with the teachings of the present invention:

TABLE 1

| Class | Examples |
| --- | --- |
| Antioxidants | Lazaroid, Probucol, Vitamin E |
| Anti-arrhythmics | Propranolol, digoxin |
| Antihypertensive Agents | Diltiazem, Nifedipine, Verapamil, Prazosin |
| Vasodilators | Nitroglycerin, Isosorbide Dinitrate |
| Vasoconstrictors | norepinephrine |
| Antiinflammatory Agents | Glucocorticoids, Cyclosporine, NSAIDS |
| Growth Factor Antagonists | Angiopeptin, trapidil, suramin |
| Antiplatelet Agents | Aspirin, Dipyridamole, Ticlopidine, Clopidogrel, GP IIb/IIIa inhibitors, Abciximab |
| Anticoagulant Agents | Heparin (low molecular weight and unfractionated), Wafarin, Hirudin |

TABLE 1-continued

| Class | Examples |
| --- | --- |
| Thrombolytic Agents | Alteplase, Reteplase, Streptase, Urokinase, TPA |
| Drugs to Alter Lipid Metabolism (e.g. statins) | Pluvastatin, Colestipol, Lovastatin |
| ACE Inhibitors | Elanapril, Fosinopril, Cilazapril |
| Antiproliferatives and Antineoplastics | Cochicine, mitomycin C, Rapamycin, paclitaxel, Everolimus, Tacrolimus, Sirolimus |
| Cell adhesion/signaling molecules | RGD-containing peptides |
| Tissue growth stimulants | Bone morphogeneic protein, fibroblast growth factor, vascular endothelial growth factor |
| Gasses | Nitric oxide, Super Oxygenated $O_2$ |
| Promotion of hollow organ occlusion or thrombosis | Alcohol, Surgical Sealant Polymers, Polyvinyl particulates, 2-Octyl Cyanoacrylate, Hydrogels, Collagen |
| Functional Protein/Factor Delivery | Insulin, Human Growth Hormone, Estrogen, Nitric Oxide |
| Second messenger targeting | Protein kinase inhibitors |
| Angiogenic | Angiopoetin, VEGF |
| Anti-Angiogenic | Endostatin |
| Inhibition of Protein Synthesis | Halofuginone |
| Antiinfective Agents | Penicillin, gentamycin, quorum-signalling modifiers |
| Gene Delivery | Genes for Nitric Oxide Synthase, human growth hormone, antisense oligonucleotides |
| Local Tissue Perfusion | Alcohol, $H_2O$, Saline, Hot or Cold $H_2O$ for thermal ablation |
| Nitric Oxide Donating Derivatives | NCX 4016-Nitric Oxide donating derivative of Aspirin |
| Contrast Media | Iopromide, iohexol |
| Microspheres | Polylactic acid microspheres, poly(lactide-co-glycolide) microspheres, poly(fumaric-co-sebacic) anhydride microspheres |
| Nanparticles/Nanspheres | Nanoparticlized paclitaxel |
| Microdelivery Devices | Rods, hemispheres, particles |
| Liposomes | phospholipid liposomes |
| Cells | Endothelial cells |
| Bacteria | Acidophilus |
| Viruses | Adenovirus gene delivery |
| Hormones | Estrogens, progesterone |
| Slurries | Cephalosporin suspension |
| Polymers | Polylactic acid |
| Polynucleotides | Naked DNA, Antisense compounds, and modifications thereof. |
| Materials | Either biodegradable or non-biodegradable, with bioactive compound covalently bound thereto. |

The use of such wettable liquids make it possible for the delivery matrix to serve as the lubricant/extrusion aid during mixing, extrusion, and/or expansion.

Optionally, further steps of the preferred embodiment of the invention may include removing the second wettable liquid. Although removal can be accomplished at room temperature, heating to an elevated temperature accelerates removal of the second wettable liquid. However, heating may not be possible to the extent otherwise allowable with non-drug and non-agent liquids if the first and/or second wettable liquids instead include drugs or agents that are susceptible to heat, in which case an alternate method may be used such as extraction with a more volatile solvent. Optional heating, for example to 320° C., can be performed following removal of the second wettable liquid. Heating may optionally be sufficient to cause sintering, typically at about 360° C., thereby locking in the microstructure. Alternatively, sintering, step 150, may be conducted after heating.

A further alternative of some of the above-disclosed embodiments involves a second stretching step . As discussed above, this second stretching step may involve heating prior to or during stretching and may be conducted in the machine direction, a transverse direction, or any combination or sequential application thereof. Sintering may optionally be performed after the second stretching.

Some embodiments of the invention differ from others, at least in part, by stretching of the expandable polymer without a drug before rewetting with a second wettable liquid that contains a drug. Because a second wettable liquid has not been applied, it is preferable that stretching be performed with heat, for example in radiant heat oven set to approximately 705° F., thereby allowing greater stretch ratios. Rewetting is then performed by applying a second wettable liquid to the expandable polymer. As previously discussed, a wettable liquid may be applied to the expandable polymer in a variety of ways. In addition, the wettable liquids applied can incorporate one or more drugs or agents in one or both of the first and second wettable liquids. For example, in instances of heating during stretching, the drug or agent can be introduced with the second wettable liquid used during the expansion step . This avoids the higher temperatures of the heating step , and thus avoids degradation of a drug or agent within the wettable liquid. If the drug or agent in the wettable liquid could withstand the heating step , the drug or agent can be included in that step as well.

The drug delivery system can be loaded with concentrations significantly greater than known coating technologies. The lubricant content in the present invention can vary over a relatively large range, for example, from about 3% to about 40% by weight. The drug or agent can be loaded during the mixing step according to weight, and is not limited by volume or surface area as it otherwise would be in conventional immersion or impregnation step s. Therefore, the drug delivery system can be loaded with drug or agent concentrations of significantly higher amounts.

Further, the release of the drug or agent can occur over relatively longer periods of time. In accordance with the present invention, it has been shown that the resulting material can emit a drug or agent for at least a period of about 4 weeks.

The techniques of the present invention may be employed to create implantable prosthetic devices that are adapted for delivery of bioactive materials. For example, vascular grafts with multiple lumens may be created using the techniques described herein. The physical structure components in such prosthetic devices is discussed in further in detail U.S. Pat. No. 5,411,550, entitled "Implantable Prosthetic Device for the Delivery of a Bioactive Material," the contents of which are incorporated herein by reference.

Controlled release systems can be described as including methods for delivering drugs or agents in a controlled manner (i.e., a specific rate of release to a localized or targeted site). Site specific controlled drug delivery can apply an effective concentration of drug or agent to a diseased locale without systemic side affects that often accompany exposure to larger doses of drugs. Patients are exposed to lower overall concentrations of drugs or agents in controlled release systems relative to systemic dosage levels. Furthermore, the drugs and agents are more effective when delivered to the specific locations requiring treatment.

The embodiments of the present invention make use of wettable liquids to form the expanded polymers. These wettable liquids can include drugs and/or other agents that can be used to treat conditions in a controlled and targeted manner.

The extruded article that contains a drug or agent can be processed into a radial and/or longitudinal expanded material using the methods of the present invention. The expanded porous article containing the drug or agent then serves as a means to deliver the drug or agent in a site-specific manner. For example, in the case of vascular grafts, the drug or agent may be a pharmacological agent directed to address infection and/or hyperplasia. In another example, the expanded polymer can be used to form or encompass a stent. In such an instance, the drug or agent can be directed to address restenosis.

Figure 21A:
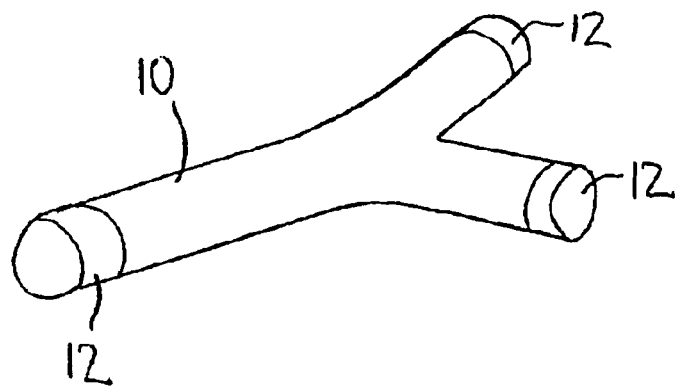
FIGS. 21A, 21B, and 21C are perspective illustrations of example medical devices that can be formed with the article formed by the present invention.

More specifically, as shown in FIG. 21A, an ultra thin wall tube 10 can be produced that can be shaped around a vascular graft 12 in a sleeve or liner fashion, which will release the drug or agent. The vascular graft 12 is formed into a desired graft shape as a part of the wetting and re-wetting process.

Figure 21B:
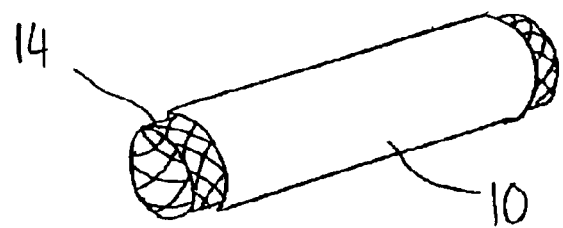
Figure 21C:
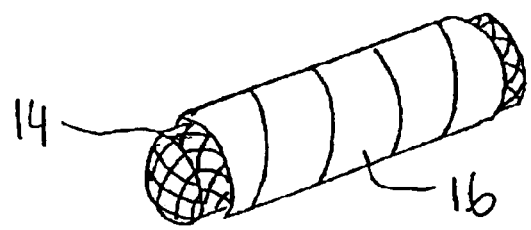

Likewise, as shown in FIG. 21B, the ultra thin wall tube 10 can wrap or slip over a stent 14, and release the drug or agent to the site-specific locale requiring treatment. The thin wall tube 10 is formed using the process of the present invention, and then slipped over a stent 14 structure. Alternatively, if the ultra thin wall is in the form of a wrap, it can wrap around the stent 14, as shown in FIG. 21C.

The inclusion of a drug or agent in the expanded polymer as made possible by the method of the present invention eliminates, or at least greatly reduces, systemic responses associated with traditional oral or intravenous therapies. The minimization of drug permeability effects through tissue results from the ability to target the application of the drug or agent to specific locales. The ability to incorporate the drug or agent in the expanded polymer makes it possible to load the drug delivery system with concentrations significantly greater than known coating technologies. Further, the release of the drug or agent can occur over longer periods of time. The use of the expanded polymer including the drug or agent provides a material that is radially expandable without splitting or breakage.

Expandable polymers of the present invention have wide ranging applications, such as devices for in vivo implantation, prostheses intended for placement or implantation to supplement or replace a segment of a natural biological blood vessel, and supports for tissue repair, reinforcement or augmentation. Specific products include but are not limited to heart valves, sutures, vascular access devices, vascular grafts, shunts and catheters. Other products include single and multilayered membranes. Multilayered membranes containing regions of selective porosity and chemistry are useful in the medical diagnostic and the filtration industries. For example, some clinical diagnostic test strips contain multilayer membranes with selective binding sites in each layer to capture analytes from blood, serum, and the like, when the test liquid is flowing through it.

According to additional aspects of the invention, expandable polymers may be formed into sheets, grafts, electrical insulation, and other known polymer applications. These applications include among other devices, vascular grafts, endovascular liners and grafts, prosthetic patches, vascular access devices, shunts, catheters, sutures or implantable tissue augmentation devices, such as those used in cosmetic surgery. According to yet a further feature, the articles of manufacture include single and multilayered membranes formed from sheets. Such membranes may be employed in clinical diagnostic test strips or in filtration devices.

The invention can be applied to other processes where stretching or expanding of material is involved. It will thus be seen that the invention efficiently attains the objects set forth above, including providing implantable devices having tailored porosity and/or chemistry characteristics. Since certain changes may be made in the above constructions and the described methods without departing from the scope of the invention, it is intended that all matter contained in the above description or shown in the accompanying drawings be interpreted as illustrative and not in a limiting sense. By way of example, any known methods for varying the porosity and/or chemistry characteristics of implantable prostheses, such as varying the lubrication level in the blended pasted, viewed in combination with the disclosed methods are considered to be within the scope of the present invention. Additionally, any methods for combining resins, pastes, billets or extrudates, according to the methods of the invention, are also considered to be within the scope of the present invention.

What is claimed is:

1. A method for forming an article, comprising:

mixing a polymer resin with a first wettable liquid and at least one of a drug and an agent to form a mixture;

forming a pre-form from the mixture; and extruding the pre-form to form the article.

2. The method according to claim 1, wherein said article is in the shape of a tube or a flat sheet.

3. The method according to claim 1, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

4. The method according to claim 1, wherein the first wettable liquid is formed of at least one of a drug and an agent.

5. The method according to claim 1, further comprising mixing a powder formed at least partially of at least one of a drug and an agent to form the polymer resin.

6. A method for forming an article, comprising:

mixing a polymer resin with a first wettable liquid and at least one of a drug and an agent to form a mixture;

forming a pre-form from the mixture;

extruding the pre-form to form an extruded article; and stretching the extruded article to form the article.

7. The method according to claim 6, wherein the article is in the shape of a tube or a flat sheet.

8. The method according to claim 6, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

9. The method according to claim 6, wherein the first wettable liquid is formed of at least one of a drug and an agent.

10. The method according to claim 6, further comprising mixing a powder formed at least partially of at least one of a drug and an agent to form the polymer resin.

11. A method for forming an article, comprising:

mixing a polymer resin with a first wettable liquid and at least one of a drug and an agent to form a mixture;

forming a pre-form from the mixture;

extruding the pre-form to form an extruded article;

drying the extruded article; and stretching the extruded article to form the article.

12. The method according to claim 11, wherein the article is in the shape of a tube or a flat sheet.

13. The method according to claim 11, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

14. The method according to claim 11, wherein the first wettable liquid is formed of at least one of a drug and an agent.

15. The method according to claim 11, further comprising mixing a powder formed at least partially of at least one of a drug and an agent to form the polymer resin.

16. A method for forming an article, comprising:

mixing a polymer resin with a first wettable liquid and at least one of a drug and an agent to form a mixture;

forming a pre-form from the mixture;

extruding the pre-form to form an extruded article;

re-wetting the extruded article with at least one of the first wettable liquid and a second wettable liquid; and stretching the re-wetted article to form the article.

17. The method according to claim 16, wherein the article is in the shape of a tube or a flat sheet.

18. The method according to claim 16, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

19. The method according to claim 16, wherein the first wettable liquid is formed of at least one of a drug and an agent.

20. The method according to claim 16, wherein the second wettable liquid is formed of at least one of a drug and an agent.

21. The method according to claim 16, further comprising mixing a powder formed at least partially of at least one of a drug and an agent to form the polymer resin.

22. A method for forming an article, comprising:
mixing a polymer resin with a first wettable liquid and at least one of a drug and an agent to form a mixture;
forming a pre-form from the mixture;
extruding the pre-form to form an extruded article;
stretching the extruded article; and
re-wetting the extruded article with a second wettable liquid to form the article.

23. The method according to claim 22, wherein the article is in the shape of a tube or a flat sheet.

24. The method according to claim 22, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

25. The method according to claim 22, wherein the first wettable liquid is formed of at least one of a drug and an agent.

26. The method according to claim 22, wherein the second wettable liquid is formed of at least one of a drug and an agent.

27. The method according to claim 22, further comprising mixing a powder formed at least partially of at least one of a drug and an agent to form the polymer resin.

28. A method for forming an article, comprising:
mixing a polymer resin with a first wettable liquid and at least one of a drug and an agent to form a mixture;
forming a pre-form from the mixture;
extruding the pre-form to form an extruded article;
stretching the extruded article;
re-wetting the extruded article with a second wettable liquid to form a re-wetted extruded article; and
stretching the re-wetted extruded article to form the article.

29. The method according to claim 28, wherein the article is in the shape of a tube or a flat sheet.

30. The method according to claim 28, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

31. The method according to claim 28, wherein the first wettable liquid is formed of at least one of a drug and an agent.

32. The method according to claim 28, wherein the second wettable liquid is formed of at least one of a drug and an agent.

33. The method according to claim 28, further comprising mixing a powder formed at least partially of at least one of a drug and an agent to form the polymer resin.

34. A method for forming an article, comprising:
mixing an aqueous dispersion of fluoropolymer with at least one of a drug and an agent to form a mixture;
coagulating the mixture;
forming a pre-form from the mixture; and
extruding the pre-form to form the article.

35. The method according to claim 34, wherein the article is in the shape of a tube or a flat sheet.

36. The method according to claim 34, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

37. A method for forming an article, comprising:
mixing an aqueous dispersion of fluoropolymer with at least one of a drug and an agent to form a mixture;

coagulating the mixture;
forming a pre-form from the mixture;
extruding the pre-form to form an extruded article; and
stretching the extruded article to form the article.

38. The method according to claim 37, wherein the article is in the shape of a tube or a flat sheet.

39. The method according to claim 37, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

40. A method for forming an article, comprising:
mixing an aqueous dispersion of fluoropolymer with at least one of a drug and an agent to form a mixture;
coagulating the mixture;
forming a pre-form from the mixture;
extruding the pre-form to form an extruded article;
drying the extruded article; and
stretching the extruded article to form the article.

41. The method according to claim 40, wherein the article is in the shape of a tube or a flat sheet.

42. The method according to claim 40, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

43. A method for forming an article, comprising:
mixing an aqueous dispersion of fluoropolymer with at least one of a drug and an agent to form a mixture;
coagulating the mixture;
forming a pre-form from the mixture;
extruding the pre-form to form an extruded article;
re-wetting the extruded article with a first wettable liquid; and
stretching the re-wetted article to form the article.

44. The method according to claim 43, wherein the article is in the shape of a tube or a flat sheet.

45. The method according to claim 43, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

46. The method according to claim 43, wherein the first wettable liquid is formed of at least one of a drug and an agent.

47. A method for forming an article, comprising:
mixing an aqueous dispersion of fluoropolymer with at least one of a drug and an agent to form a mixture;
coagulating the mixture;
forming a pre-form from the mixture;
extruding the pre-form to form an extruded article;
stretching the extruded article; and
re-wetting the extruded article with a first wettable liquid to form the article.

48. The method according to claim 47, wherein the article is in the shape of a tube or a flat sheet.

49. The method according to claim 47, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

50. The method according to claim 47, wherein the first wettable liquid is formed of at least one of a drug and an agent.

51. A method for forming an article, comprising:
mixing an aqueous dispersion of fluoropolymer with at least one of a drug and an agent to form a mixture;
coagulating the mixture;
forming a pre-form from the mixture;
extruding the pre-form to form an extruded article;
stretching the extruded article;
re-wetting the extruded article with a first wettable liquid; and stretching the re-wetted article to form the article.

52. The method according to claim 51, wherein the article is in the shape of a tube or a flat sheet.

53. The method according to claim 51, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

54. The method according to claim 51, wherein the first wettable liquid is formed of at least one of a drug and an agent.

55. A method for forming an article, comprising:
mixing a polymer resin with a first wettable liquid and at least one of a drug and an agent to form a mixture;
forming a pre-form from the mixture;
extruding the pre-form to form an extruded article;
stretching the extruded article; and
re-wetting the extruded article with a second wettable liquid including at least one of a drug and an agent to form the article.

56. The method according to claim 55, wherein the article is in the shape of a tube or a flat sheet.

57. The method according to claim 55, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

58. The method according to claim 55, wherein the first wettable liquid is formed of at least one of a drug and an agent.

59. The method according to claim 55, wherein the second wettable liquid is formed of at least one of a drug and an agent.

60. The method according to claim 55, further comprising mixing a powder formed at least partially of at least one of a drug and an agent to form the polymer resin.

61. A method for forming an article, comprising:
mixing a polymer resin with a first wettable liquid and at least one of a drug and an agent to form a mixture;
forming a pre-form from the mixture;
extruding the pre-form to form an extruded article;
stretching the extruded article;
re-wetting the extruded article with a second wettable liquid including at least one of a drug and an agent; and
stretching the re-wetted extruded article to form the article.

62. The method according to claim 61, wherein the article is in the shape of a tube or a flat sheet.

63. The method according to claim 61, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

64. The method according to claim 61, wherein the first wettable liquid is formed of at least one of a drug and an agent.

65. The method according to claim 61, wherein the second wettable liquid is formed of at least one of a drug and an agent.

66. The method according to claim 61, further comprising mixing a powder formed at least partially of at least one of a drug and an agent to form the polymer resin.

67. A method for forming an article, comprising:
combining at least one of a drug and an agent with a first wettable liquid;
mixing a polymer resin with the first wettable liquid to form a mixture;
forming a pre-form from the mixture;
extruding the pre-form to form an extruded article;
drying a low BP component of the wettable liquid from the extruded article; and
stretching the extruded article to form the article.

68. The method according to claim 67, wherein the article is in the shape of a tube or a flat sheet.

69. The method according to claim 67, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

70. The method according to claim 67, wherein the first wettable liquid is formed of at least one of a drug and an agent.

71. The method according to claim 67, wherein the second wettable liquid is formed of at least one of a drug and an agent.

72. The method according to claim 67, further comprising mixing a powder formed at least partially of at least one of a drug and an agent to form the polymer resin.

73. A method for forming an article, comprising:
mixing a polymer resin with a first wettable liquid and at least one of a drug and an agent to form a mixture;
forming a pre-form from the mixture;
extruding the pre-form to form an extruded article;
drying a low BP component of the first wettable liquid from the extruded article; and
stretching the extruded article to form the article.

74. The method according to claim 73, wherein the article is in the shape of a tube or a flat sheet.

75. The method according to claim 73, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

76. The method according to claim 73, wherein the first wettable liquid is formed of at least one of a drug and an agent.

77. The method according to claim 73, further comprising mixing a powder formed at least partially of at least one of a drug and an agent to form the polymer resin.

78. A method for forming an article, comprising:
mixing a polymer resin with a first wettable liquid to form a mixture;
forming a pre-form from the mixture;
extruding the pre-form to form an extruded article;
re-wetting the extruded article with at least one of the first wettable liquid and a second wettable liquid, the second wettable liquid formed at least partially with at least one of a drug and an agent; and
stretching the re-wetted article to form the article.

79. The method according to claim 78, wherein the article is in the shape of a tube or a flat sheet.

80. The method according to claim 78, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

81. The method according to claim 78, wherein the first wettable liquid is formed of at least one of a drug and an agent.

82. The method according to claim 78, further comprising mixing a powder formed at least partially of at least one of a drug and an agent to form the polymer resin.

83. A method for forming an article, comprising:
mixing a polymer resin with a first wettable liquid to form a mixture;
forming a pre-form from the mixture;
extruding the pre-form to form an extruded article;
stretching the extruded article; and
re-wetting the extruded article with a second wettable liquid to form the article, wherein the second wettable liquid is formed at least partially with at least one of a drug and an agent.

84. The method according to claim 83, wherein the article is in the shape of a tube or a flat sheet.

85. The method according to claim 83, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

86. The method according to claim 83, wherein the first wettable liquid is formed of at least one of a drug and an agent.

87. The method according to claim 83, further comprising mixing a powder formed at least partially of at least one of a drug and an agent to form the polymer resin.

88. A method for forming an article, comprising:
mixing a polymer resin with a first wettable liquid to form a mixture;
forming a pre-form from the mixture;
extruding the pre-form to form an extruded article;
stretching the extruded article;
re-wetting the extruded article with a second wettable liquid to form a re-wetted extruded article, the second wettable liquid formed at least partially with at least one of a drug and an agent; and
stretching the re-wetted extruded article to form the article.

89. The method according to claim 88, wherein the article is in the shape of a tube or a flat sheet.

90. The method according to claim 88, wherein the at least one of a drug and an agent comprise at least one of anti-arrhythmics, antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, cell adhesion/signaling molecules, nitric oxide donating derivatives, contrast media, microspheres, nanoparticles, nanospheres, microdelivery devices, liposomes, cells, bacteria, viruses, hormones, slurries, polymers, polynucleotides, vasodialators, vasoconstrictors, and materials with a bioactive compound covalently bound thereto.

91. The method according to claim 88, wherein the first wettable liquid is formed of at least one of a drug and an agent.

92. The method according to claim 88, further comprising mixing a powder formed at least partially of at least one of a drug and an agent to form the polymer resin.

* * * * *